United States Patent
Cao et al.

(10) Patent No.: US 11,532,083 B2
(45) Date of Patent: *Dec. 20, 2022

(54) SYSTEMS AND METHODS FOR DETERMINING A REGION OF INTEREST IN MEDICAL IMAGING

(71) Applicant: SHANGHAI UNITED IMAGING HEALTHCARE CO., LTD., Shanghai (CN)

(72) Inventors: Jianhui Cao, Shanghai (CN); Lei Zhang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 114 days.

This patent is subject to a terminal disclaimer.

(21) Appl. No.: 17/087,592

(22) Filed: Nov. 2, 2020

(65) Prior Publication Data

US 2021/0049765 A1    Feb. 18, 2021

Related U.S. Application Data

(63) Continuation of application No. 16/003,609, filed on Jun. 8, 2018, now Pat. No. 10,825,170, which is a
(Continued)

(51) Int. Cl.
*G06T 7/00* (2017.01)
*A61B 5/11* (2006.01)
(Continued)

(52) U.S. Cl.
CPC .......... *G06T 7/0012* (2013.01); *A61B 5/0037* (2013.01); *A61B 5/015* (2013.01);
(Continued)

(58) Field of Classification Search
CPC ......... G06T 7/0012; G06T 7/521; G06T 7/75; G06T 17/00; G06T 2200/08;
(Continued)

(56) References Cited

U.S. PATENT DOCUMENTS 6,323,942 B1 * 11/2001 Bamji .................... G01S 17/89
  356/5.01
2003/0136201 A1 * 7/2003 Hubbard, Jr. ............ A43B 3/00
  73/862.41
(Continued)

FOREIGN PATENT DOCUMENTS

CN    102997866 A    3/2013
CN    204863247 U    12/2015
(Continued)

OTHER PUBLICATIONS

International Search Report in PCT/CN2017/120280 dated Sep. 6, 2018, 4 pages.
(Continued)

*Primary Examiner* — Amandeep Saini
(74) *Attorney, Agent, or Firm* — Metis IP LLC

(57) ABSTRACT

A method for determining an ROI in medical imaging may include receiving first position information related to a body contour of a subject with respect to a support from a flexible device configured with a plurality of position sensors. The flexible device may be configured to conform to the body contour of the subject, and the support may be configured to support the subject. The method may also include generating a 3D model of the subject based on the first position information. The method may further include determining an ROI of the subject based on the 3D model of the subject.

20 Claims, 18 Drawing Sheets

Related U.S. Application Data continuation of application No. PCT/CN2017/120280, filed on Dec. 29, 2017.

(51) Int. Cl.

| | | |
|---|---|---|
| *G06T 7/521* | (2017.01) | |
| *G06T 7/73* | (2017.01) | |
| *G06T 17/00* | (2006.01) | |
| *A61B 5/107* | (2006.01) | |
| *A61B 5/103* | (2006.01) | |
| *A61B 5/00* | (2006.01) | |
| *A61B 5/055* | (2006.01) | |
| *A61B 5/01* | (2006.01) | |

(52) U.S. Cl.
CPC ............ *A61B 5/055* (2013.01); *A61B 5/1036* (2013.01); *A61B 5/1072* (2013.01); *A61B 5/1077* (2013.01); *A61B 5/1114* (2013.01); *A61B 5/1115* (2013.01); *A61B 5/1127* (2013.01); *A61B 5/6802* (2013.01); *A61B 5/6887* (2013.01); *G06T 7/521* (2017.01); *G06T 7/75* (2017.01); *G06T 17/00* (2013.01); *A61B 2562/0247* (2013.01); *A61B 2562/0271* (2013.01); *G06T 2200/08* (2013.01); *G06T 2207/10081* (2013.01); *G06T 2207/10088* (2013.01); *G06T 2207/10104* (2013.01); *G06T 2207/10132* (2013.01); *G06T 2207/30004* (2013.01)

(58) Field of Classification Search
CPC . G06T 2207/10081; G06T 2207/10088; G06T 2207/10104; G06T 2207/10132; G06T 2207/30004; A61B 5/0037; A61B 5/015; A61B 5/055; A61B 5/1036; A61B 5/1072; A61B 5/1077; A61B 5/1114; A61B 5/1115; A61B 5/1127; A61B 5/6802; A61B 5/6887; A61B 2562/0247; A61B 2562/0271
USPC ........................................................ 382/128
See application file for complete search history.

(56) References Cited

U.S. PATENT DOCUMENTS

| | | |
|---|---|---|
| 2004/0081341 A1 | 4/2004 | Cherek et al. |
| 2006/0233430 A1 | 10/2006 | Kimura |
| 2013/0060146 A1 | 3/2013 | Yang et al. |
| 2013/0070995 A1* | 3/2013 | Chou ..................... G06T 7/344 382/131 |
| 2013/0083894 A1 | 4/2013 | Niebler et al. |
| 2014/0029812 A1 | 1/2014 | Kriston et al. |
| 2014/0093134 A1 | 4/2014 | Park et al. |
| 2015/0257731 A1* | 9/2015 | Abe ..................... A61B 8/0883 600/443 |
| 2015/0323388 A1* | 11/2015 | Kostic .................... A61G 13/10 250/338.1 |
| 2016/0183879 A1* | 6/2016 | Goldish ................. A61B 5/702 600/474 |
| 2017/0086758 A1 | 3/2017 | Mc Carthy et al. |
| 2017/0100089 A1* | 4/2017 | Chang .................. A61B 6/0492 |
| 2017/0143304 A1 | 5/2017 | Malik et al. |
| 2017/0154505 A1* | 6/2017 | Kim ...................... A61B 5/1114 |
| 2017/0181809 A1 | 6/2017 | Panescu et al. |
| 2017/0188011 A1* | 6/2017 | Panescu ............... A61B 1/00009 |
| 2017/0256069 A1* | 9/2017 | Link ..................... H04N 5/2226 |
| 2017/0312065 A1* | 11/2017 | Marshall ................ A61B 5/682 |
| 2017/0325683 A1* | 11/2017 | Larson .................. G16H 50/30 |
| 2017/0354385 A1 | 12/2017 | Lerch |
| 2018/0260967 A1* | 9/2018 | Bleyer ..................... G06T 7/521 |
| 2020/0229737 A1 | 7/2020 | Hao et al. |

FOREIGN PATENT DOCUMENTS

| | | |
|---|---|---|
| CN | 205658920 U | 10/2016 |
| CN | 205849464 U | 1/2017 |
| CN | 107358607 A | 11/2017 |
| WO | 2006109308 A1 | 10/2006 |
| WO | 2012122002 A1 | 9/2012 |
| WO | 2019127365 A1 | 7/2019 |

OTHER PUBLICATIONS

Written Opinion in PCT/CN/2017/120280 dated Sep. 6, 2018, 4 pages.
International Search Report in PCT/CN2017/119896 dated Sep. 20, 2018, 4 pages.
Written Opinion in PCT/CN2017/119896 dated Sep. 20, 2018, 4 pages.

* cited by examiner

1100

```
┌─────────────────────────────────────────────────┐
│ Receiving distance information from a body      │
│ contour of a subject to a light pulse           │ ~ 1102
│ generator, the distance information being       │
│ determined based on time of flight (TOF)        │
│ information associated with light pulses        │
│ emitted by the light pulse generator toward     │
│ the subject                                     │
└─────────────────────────────────────────────────┘
                        ↓
┌─────────────────────────────────────────────────┐
│ Generating, based on the TOF information, a 3D  │ ~ 1104
│ model of the subject                            │
└─────────────────────────────────────────────────┘
                        ↓
┌─────────────────────────────────────────────────┐
│ Determining, based on the 3D model of the       │ ~ 1106
│ subject, an ROI of the subject                  │
└─────────────────────────────────────────────────┘
                        ↓
┌─────────────────────────────────────────────────┐
│ Sending an instruction to an imaging device to  │ ~ 1108
│ scan a target portion of the subject including  │
│ the ROI of the subject                          │
└─────────────────────────────────────────────────┘
```

FIG. 11

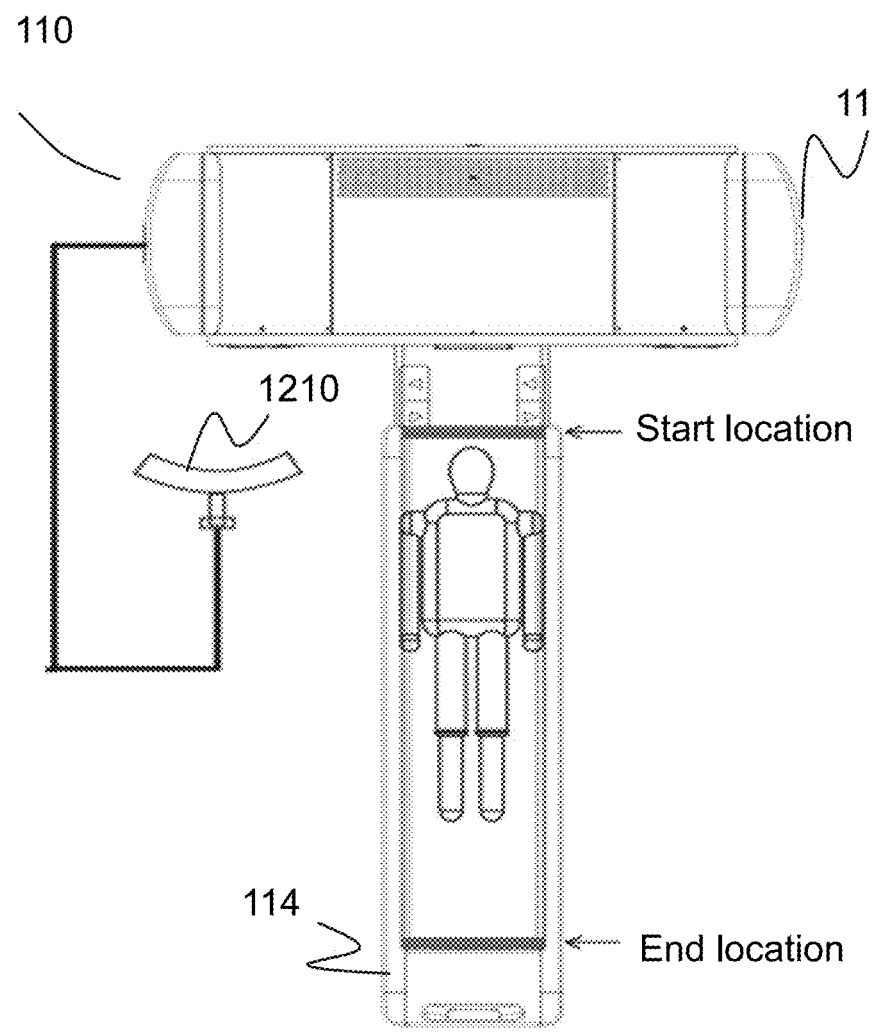
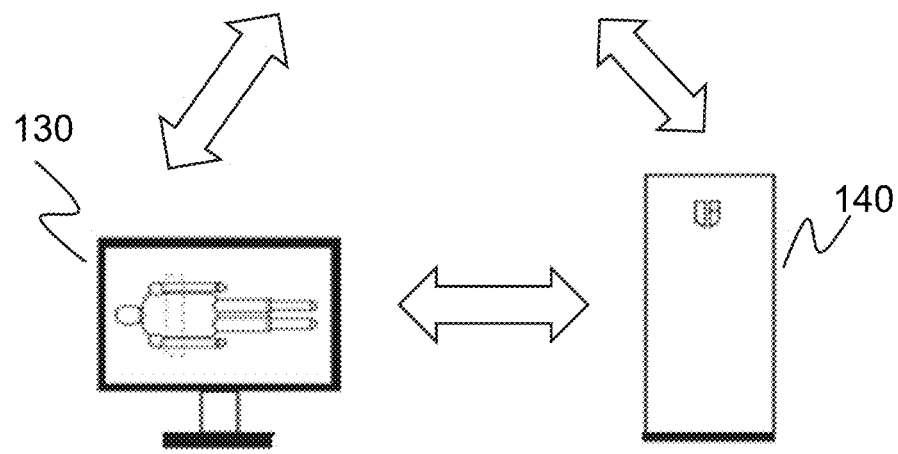
FIG. 12

SYSTEMS AND METHODS FOR DETERMINING A REGION OF INTEREST IN MEDICAL IMAGING

CROSS-REFERENCE TO RELATED APPLICATION

This application is a Continuation of U.S. patent application Ser. No. 16/003,609 filed on Jun. 8, 2018, which is a Continuation of International Application No. PCT/CN/2017/120280, filed on Dec. 29, 2017.

TECHNICAL FIELD

The present disclosure generally relates to medical imaging, and more particularly, relates to systems and methods for determining a position of a region of interest (ROI) in medical imaging.

BACKGROUND

Medical imaging technology has been widely used for clinical examination and medical diagnosis in recent years. When using a medical imaging device to perform a scan, an operator (e.g., a doctor, a technician, etc.) needs to determine a position of an ROI of a patient for scanning. The position of the ROI may be determined by the operator with the help of a pre-scanned image of the patient. The pre-scanning on the patent requires extra time and energy of the operator. The efficiency of the medical imaging process may be decreased. Further, a pre-scanning on the patient may cause extra and unnecessary radiation to the patient. Therefore, it is desirable to develop systems and methods for determining an ROI of a patient for scanning in medical imaging efficiently and effectively.

SUMMARY

According to an aspect of the present disclosure, a system for determining an ROI in medical imaging is provided. The system may include a storage device storing a set of instructions, and at least one processor in communication with the storage device. When executing the set of instructions, the at least one processor may be configured to cause the system to receive, from a flexible device configured with a plurality of position sensors, first position information related to a body contour of a subject with respect to a support. The flexible device may be configured to conform to the body contour of the subject. The support may be configured to support the subject. The at least one processor may cause the system to generate, based on the first position information, a 3-dimensional (3D) model of the subject. The at least one processor may also cause the system to determine, based on the 3D model of the subject, an ROI of the subject.

In some embodiments, the flexible device may include a plurality of units arranged in an array. Each of the plurality of units may include one or more position sensors of the plurality of position sensors. Each pair of adjacent units of the plurality of units may be connected to each other via a flexible connector.

In some embodiments, a unit of the plurality of units may include a first layer covering the one or more position sensors of the unit.

In some embodiments, the unit of the plurality of units may further include a second layer. The one or more position sensors of the unit may be sandwiched between the first layer and the second layer.

In some embodiments, at least one of the first layer or the second lay may be made of a compound of artificial fiber and plant fiber.

In some embodiments, to determine the ROI of the subject, the at least one processor may be further configured to cause the system to determine, based on the 3D model of the subject, a position of the ROI inside the subject. The at least one processor may also cause the system to obtain second position information of the subject with respect to the imaging device. The at least one processor may determine, based on the position of the ROI inside the subject and the second position information, the ROI of the subject.

In some embodiments, at least part of the second information may be acquired from an image acquisition device or a plurality of pressure sensors configured in the support.

In some embodiments, to determine the position of the ROI inside the subject, the at least one processor may be configured to cause the system to acquire information associated with thermal distribution of the subject. The at least one processor may also determine, based on the 3D model of the subject and the information associated with thermal distribution of the subject, the position of the ROI inside the subject.

In some embodiments, at least one of the flexible device or the support may include one or more thermal sensors, and at least part of the information associated with thermal distribution of the subject may be acquired from the one or more thermal sensors.

In some embodiments, to determine the position of the ROI inside the subject, the at least one processor may be configured to cause the system to acquire physiological data related to the subject, and acquire anatomical information associated with the subject. The at least one processor may also determine the position of the ROI inside the subject based on the 3D model of the subject, the physiological data, and anatomical information associated with the subject.

In some embodiments, the anatomical information associated with the subject may include at least one of historical anatomical information of the subject or anatomical information of one or more reference samples related to the subject.

In some embodiments, at least part of the physiological data may be acquired from the support or be determined based on the 3D model of the subject.

In some embodiments, the flexible device may be a wearable device.

According to another aspect of the present disclosure, a system for determining an ROI in medical imaging is provided. The system may include a storage device storing a set of instructions and at least one processor in communication with the storage device. When executing the set of instructions, the at least one processor may be configured to cause the system to receive one or more images of structured light projected by a projector on a subject. The at least one processor may generate, based on the one or more images of the structured light projected on the subject, a 3D model of the subject. The at least one processor may also determine, based on the 3D model of the subject, an ROI of the subject.

In some embodiments, the structured light may be at least one of structured light spot, structured light stripe, or structured light grid.

In some embodiments, the one or more images of the structured light may be received from an imaging acquisition device. The imaging device may further include an extendable pole configured to control a position of at least one of the imaging acquisition device or the projector.

In some embodiments, the projector may further include a plurality of sub-projectors arranged in an arc. Each sub-projector of the plurality of sub-projectors may be configured to project at least a portion of the structured light on the subject.

In some embodiments, the one or more images of the structured light may be received from an imaging acquisition device. The imaging acquisition device may further include a plurality of sub-imaging acquisition devices arranged in an arc. Each sub-imaging acquisition device of the plurality of sub-imaging acquisition devices may be configured to capture one of the one or more images of the structured light.

According to yet another aspect of the present disclosure, a system for determining an ROI is provided. The system may include a storage device storing a set of instructions and at least one processor in communication with the storage device. When executing the set of instructions, the at least one processor may be configured to cause the system to receive distance information from a body contour of a subject to a light pulse generator. The distance information may be determined based on time of flight (TOF) information associated with light pulses emitted by the light pulse generator toward the subject. The at least one processor may cause the system to generate, based on the TOF information, a 3D model of the subject. The at least one processor may cause the system to determine, based on the 3D model of the subject, a region of interest (ROI) of the subject.

In some embodiments, the light pulse generator may move when emitting the light pulses toward the subject. The movement of the light pulse generator may be controlled by an extendable pole of the imaging device.

In some embodiments, the light pulse generator may further include a plurality of sub-light pulse generators arranged in an arc. Each sub-light pulse generator of the plurality of sub-light pulse generators may be configured to emit at least a portion of the light pulses toward the subject.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 11 is a flowchart illustrating an exemplary process for scanning a subject by an imaging device according to some embodiments of the present disclosure;

FIG. 12 is a schematic diagram illustrating an exemplary imaging system according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise,"

"comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 2:
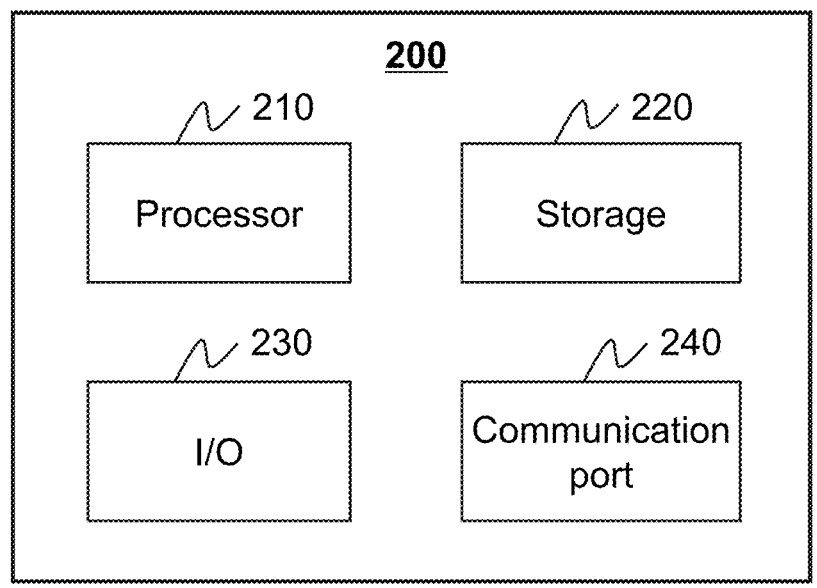
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for an imaging system. In some embodiments, the imaging system may include a single modality imaging system and/or a multi-modality imaging system. The single modality imaging system may include, for example, an X-ray imaging system, an computed tomography (CT) system, a magnetic resonance imaging (MRI) system, an ultrasonography system, a positron emission tomography (PET) system, or the like, or any combination thereof. The multi-modality imaging system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a positron emission tomography-computed tomography (PET-CT) system, a C-arm system, a digital subtraction angiography-magnetic resonance imaging (DSA-MRI) system, etc. It should be noted that the imaging system described below is merely provided for illustration purposes, and not intended to limit the scope of the present disclosure.

The present disclosure provides mechanisms (which can include methods, systems, computer-readable medium, etc.) for determining a region of interest (ROI) of a subject for medical examination. For example, the systems and/or methods provided in the present disclosure may determine a three-dimensional (3D) model of the subject, and determine the ROI based on the 3D model and/or the spatial position of the subject with respect to the imaging device. The 3D model of the subject may be determined by various ways disclosed in the present disclosure. For example, the 3D model may be determined based on a flexible device configured with a plurality of position sensors, structured light projected on the subject, time of flight (TOF) information associated with light pulses emitted toward the subject, or the like, or any combination thereof.

Figure 1:
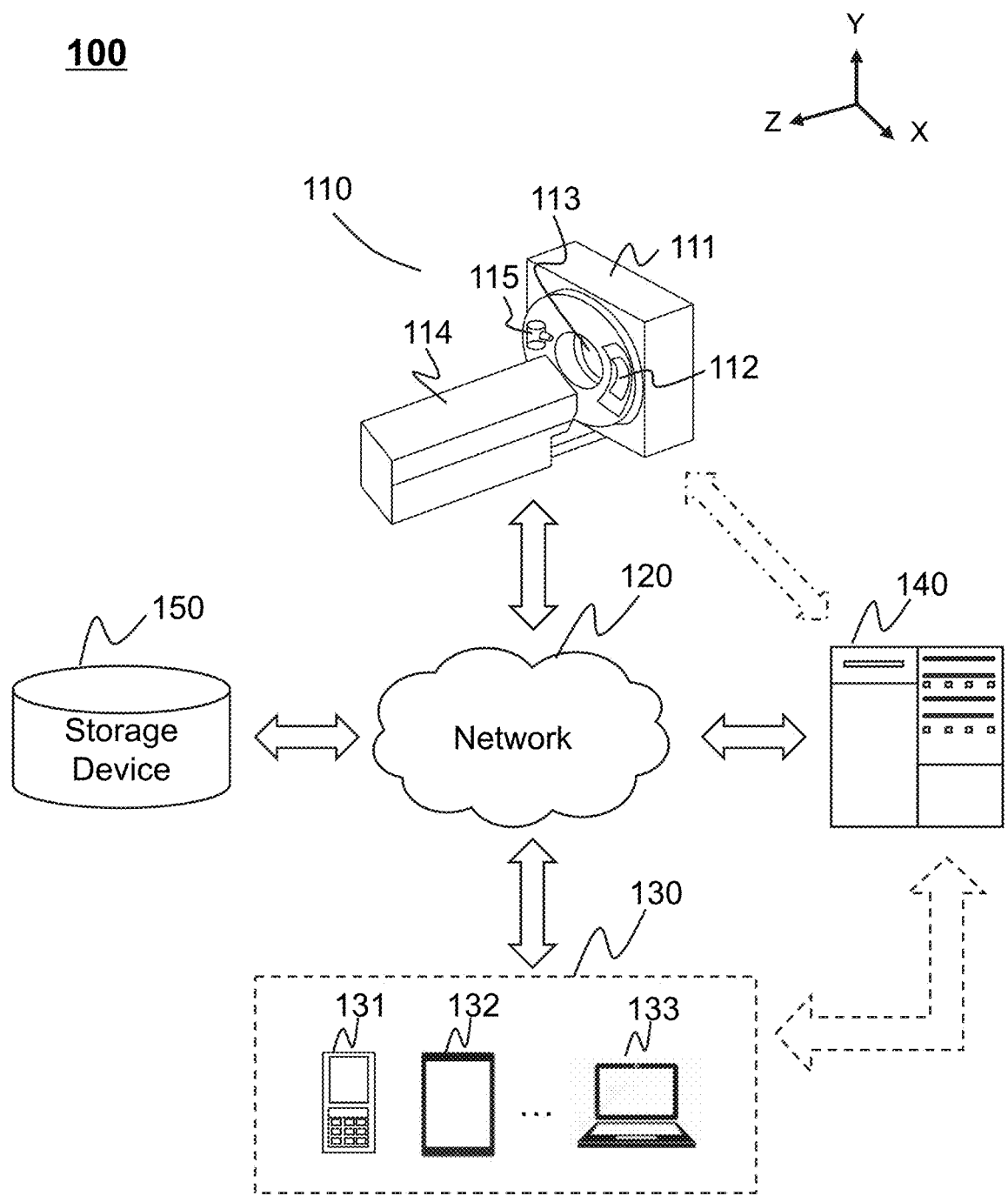
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. As shown, the imaging system 100 may include an imaging device 110, a network 120, one or more terminals 130, a processing engine 140, and a storage device 150. In some embodiments, the imaging device 110, the terminal(s) 130, the processing engine 140, and/or the storage device 150 may be connected to and/or communicate with each other via a wireless connection (e.g., the network 120), a wired connection, or a combination thereof. The connection between the components of the imaging system 100 may be variable. Merely by way of example, the imaging device 110 may be connected to the processing engine 140 through the network 120, as illustrated in FIG. 1. As another example, the imaging device 110 may be connected to the processing engine 140 directly. As a further example, the storage device 150 may be connected to the processing engine 140 through the network 120, as illustrated in FIG. 1, or connected to the processing engine 140 directly. As still a further example, a terminal 130 may be connected to the processing engine 140 through the network 120, as illustrated in FIG. 1, or connected to the processing engine 140 directly.

The imaging device 110 may generate or provide image data via scanning a subject (e.g., a patient) disposed on a scanning table of the imaging device 110. In some embodiments, the imaging device 110 may include a single-modality scanner and/or multi-modality scanner. The single-modality scanner may include, for example, a computed tomography (CT) scanner. The multi-modality scanner may include a single photon emission computed tomography-computed tomography (SPECT-CT) scanner, a positron emission tomography-computed tomography (PET-CT) scanner, a computed tomography-ultra-sonic (CT-US) scanner, a digital subtraction angiography-computed tomography (DSA-CT) scanner, or the like, or a combination thereof. In some embodiments, the image data may include projection data, images relating to the subject, etc. The projection data may be raw data generated by the imaging device 110 by scanning the subject, or data generated by a forward projection on an image relating to the subject. In some embodiments, the subject may include a body, a substance, an object, or the like, or a combination thereof. In some embodiments, the subject may include a specific portion of a body, such as a head, a thorax, an abdomen, or the like, or a combination thereof. In some embodiments, the subject may include a specific organ or region of interest, such as an esophagus, a trachea, a bronchus, a stomach, a gallbladder, a small intestine, a colon, a bladder, a ureter, a uterus, a fallopian tube, etc.

In some embodiments, the imaging device 110 may include a gantry 111, a detector 112, a detecting region 113, a scanning table 114, and a radioactive scanning source 115. The gantry 111 may support the detector 112 and the radioactive scanning source 115. A subject may be placed on the scanning table 114 to be scanned. The radioactive scanning source 115 may emit radioactive rays to the subject. The radiation may include a particle ray, a photon ray, or the like, or a combination thereof. In some embodiments, the radiation may include a plurality of radiation particles (e.g., neutrons, protons, electron, μ-mesons, heavy ions), a plurality of radiation photons (e.g., X-ray, a γ-ray, ultraviolet, laser), or the like, or a combination thereof. The detector 112 may detect radiations and/or radiation events (e.g., gamma photons) emitted from the detecting region 113. In some embodiments, the detector 112 may include a plurality of detector units. The detector units may include a scintillation detector (e.g., a cesium iodide detector) or a gas detector. The detector unit may be a single-row detector or a multi-rows detector.

In some embodiments, the imaging device 110 may be integrated with one or more other devices that may facilitate the scanning of the subject, such as, an image-recording device. The image-recording device may be configured to take various types of images related to the subject. For example, the image-recording device may be a two-dimensional (2D) camera that takes pictures of the exterior or outline of the subject. As another example, the image-recording device may be a 3D scanner (e.g., a laser scanner, an infrared scanner, a 3D CMOS sensor) that records the spatial representation of the subject.

The network 120 may include any suitable network that can facilitate exchange of information and/or data for the imaging system 100. In some embodiments, one or more components of the imaging system 100 (e.g., the imaging device 110, the processing engine 140, the storage device 150, the terminal(s) 130) may communicate information and/or data with one or more other components of the imaging system 100 via the network 120. For example, the processing engine 140 may obtain image data from the imaging device 110 via the network 120. As another example, the processing engine 140 may obtain user instruction(s) from the terminal(s) 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may be connected to and/or communicate with the imaging device 110, the processing engine 140, and/or the storage device 150. For example, the terminal(s) 130 may obtain a processed image from the processing engine 140. As another example, the terminal(s) 130 may obtain image data acquired via the imaging device 110 and transmit the image data to the processing engine 140 to be processed. In some embodiments, the terminal(s) 130 may include a mobile device 131, a tablet computer 132, a laptop computer 133, or the like, or any combination thereof. For example, the mobile device 131 may include a mobile phone, a personal digital assistance (PDA), a gaming device, a navigation device, a point of sale (POS) device, a laptop, a tablet computer, a desktop, or the like, or any combination thereof. In some embodiments, the terminal(s) 130 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing engine 140 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 130 may be part of the processing engine 140.

The processing engine 140 may process data and/or information obtained from the imaging device 110, the storage device 150, the terminal(s) 130, or other components of the imaging system 100. For example, the processing engine 140 may reconstruct an image based on projection data generated by the imaging device 110. As another example, the processing engine 140 may determine the position of a target region (e.g., a region in a patient) to be scanned by the imaging device 110. In some embodiments, the processing engine 140 may be a single server or a server group. The server group may be centralized or distributed. In some embodiments, the processing engine 140 may be local to or remote from the imaging system 100. For example, the processing engine 140 may access information and/or data from the imaging device 110, the storage device 150, and/or the terminal(s) 130 via the network 120. As another example, the processing engine 140 may be directly connected to the imaging device 110, the terminal(s) 130, and/or the storage device 150 to access information and/or data. In some embodiments, the processing engine 140 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing engine 140 may be implemented by a computing device 200 having one or more components as described in connection with FIG. 2.

The storage device 150 may store data, instructions, and/or any other information. In some embodiments, the storage device 150 may store data obtained from the processing engine 140, the terminal(s) 130, and/or the interaction device 150. In some embodiments, the storage device 150 may store data and/or instructions that the processing engine 140 may execute or use to perform exemplary methods described in the present disclosure. In some embodiments, the storage device 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 120 to communicate with one or more other components of the imaging system 100 (e.g., the processing engine 140, the terminal(s) 130). One or more components of the imaging system 100 may access the data or instructions stored in the storage device 150 via the network 120. In some embodiments, the storage device 150 may be part of the processing engine 140.

In some embodiments, a three-dimensional coordinate system may be used in the imaging system 100 as illustrated in FIG. 1. A first axis may be parallel to the lateral direction of the scanning table 114 (e.g., the X direction perpendicular to and pointing out of the paper as shown in FIG. 1). A second axis may be parallel to the longitudinal direction of the scanning table 114 (e.g., the Z direction as shown in FIG. 1). A third axis may be along a vertical direction of the scanning table 114 (e.g., the Y direction as shown in FIG. 1). The origin of the three-dimensional coordinate system may be any point in the space. The origin of the three-dimensional coordinate system may be determined by an operator. The origin of the three-dimensional coordinate system may be determined by the imaging system 100.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 150 may be a data storage including cloud computing platforms, such as, public cloud, private cloud, community, and hybrid clouds, etc. However, those variations and modifications do not depart the scope of the present disclosure.

FIG. 2 is a schematic diagram illustrating exemplary hardware and/or software components of an exemplary computing device 200 on which the processing engine 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing engine 140 in accordance with techniques described herein. The computer instructions may include, for example, routines, programs, objects, components, data structures, procedures, modules, and functions, which perform particular functions described herein. For example, the processor 210 may process image data obtained from the imaging device 110, the terminals 130, the storage device 150, and/or any other component of the imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operation s A and B).

The storage 220 may store data/information obtained from the imaging device 110, the terminals 130, the storage device 150, and/or any other component of the imaging system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing engine 140 for determining the position of a target region of a subject (e.g., a target portion of a patient).

The I/O 230 may input and/or output signals, data, information, etc. In some embodiments, the I/O 230 may enable a user interaction with the processing engine 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing engine 140 and the imaging device 110, the terminals 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
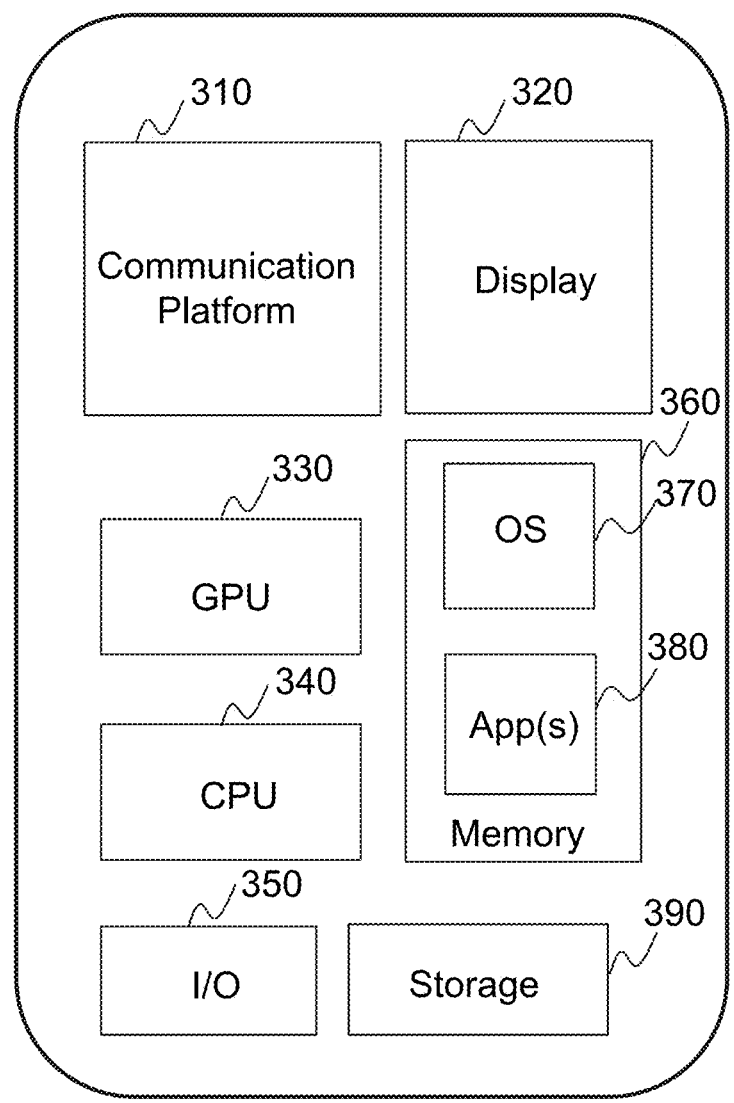
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 on which the terminals 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing engine 140. User interactions with the information stream may be achieved via the I/O 350 and provided to the processing engine 140 and/or other components of the imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
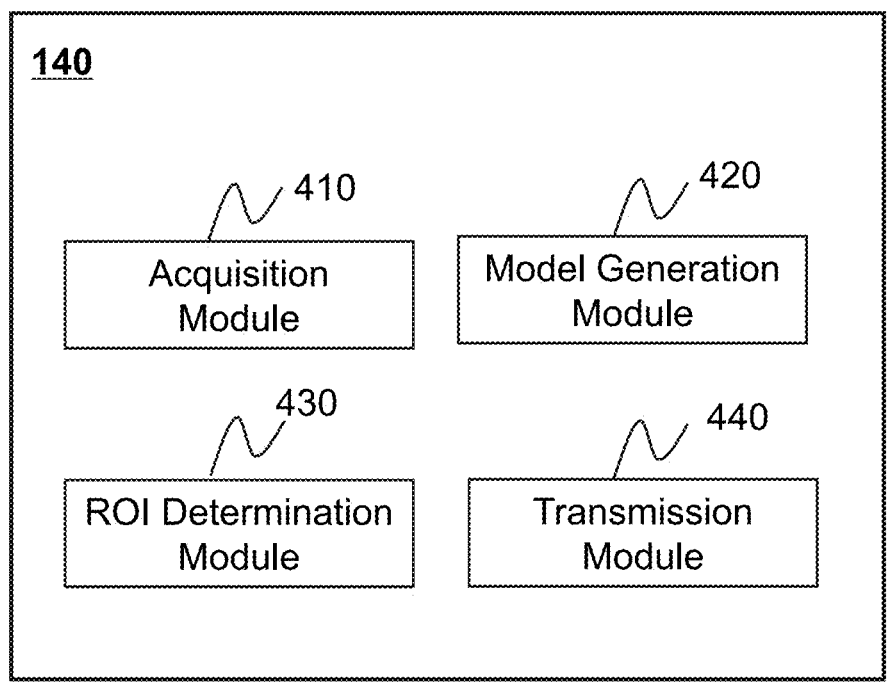
FIG. 4 is a block diagram illustrating an exemplary processing engine according to some embodiments of the present disclosure.

FIG. 4 is a block diagram illustrating an exemplary processing engine 140 according to some embodiments of the present disclosure. As illustrated in FIG. 4, the processing engine 140 may include an acquisition module 410, a model generation module 420, an ROI determination module 430, and a transmission module 440. The processing engine 140 may be implemented on various components (e.g., the processor 210 of the computing device 200 as illustrated in FIG. 2). For example, at least a portion of the processing engine 140 may be implemented on a computing device as illustrated in FIG. 2 or a mobile device as illustrated in FIG. 3.

The acquisition module 410 may acquire data related to the imaging system 100. For example, the acquisition module 410 may acquire information related to a subject (e.g., a patient) to facilitate the subsequent scanning on the subject. Exemplary information related to the subject may include position information related to a body contour of the subject, an image of the subject indicating its position on the scanning table 114, information related to thermal distribution of the subject, physiological data related to the subject, anatomical information related to subject, an image of structured light projected on the subject, TOF information associated with light pulses emitted toward the subject, or the like, or any combination thereof. In some embodiments, the acquisition module 410 may acquire the information related to the imaging system 100 from one or more components of the imaging system 100, such as the imaging device 110, the storage device 150. Additionally or alternatively, the acquisition module 410 may acquire the information from an external source via the network 120.

The model generation module 420 may generate a 3D model of the subject based on information acquired from the acquisition module 410. For example, the model generation module 420 may generate the 3D model based on position information related to a body contour of the subject measured by a flexible device. As another example, the model generation module 420 may generate the 3D model based on an image of structured light projected on the subject, or TOF information associated with light pulses emitted toward the subject. In some embodiments, the model generation module 420 may generate the 3D model according to a 3D reconstruction technique, a surface fitting technique, or any other suitable technique that can be used to generate a 3D model. Exemplary 3D reconstruction techniques may include an algorithm based on boundary contours, an algorithm based on non-uniform rational B-splines (NURBS), an algorithm based on a triangulation model, etc. Exemplary surface fitting techniques may include a least squares (LS) algorithm, a moving least squares algorithm (MLS), etc.

The ROI determination module 430 may determine the position of the ROI of the subject related to the imaging device 110. The position of the ROI may be determined based on a position of the ROI with respect to the 3D model and the position of the subject with respect to the imaging device 110. In some embodiments, the position of the ROI with respect to the 3D model may be determined based on, such as physiological data, anatomic information, thermal distribution information related to the subject, and/or a pre-scanned image of the subject, or the like, or any combination thereof. The position of the subject with respect to the imaging device 110 may be determined, for example, according to an image of the subject indicating a spatial correlation between the subject and the scanning table 114, a spatial correlation between the ROI and a reference object located outside the subject.

The transmission module 440 may send information and/or an instruction to one or more components the imaging device 110. In some embodiments, the information and/or the instruction may be related to a scanning operation on the subject. For example, the information may include the position of the ROI with respect to the imaging device 110. The transmission module 440 may send an instruction to operate the imaging device 110 to adjust the position of the scanning table 114 to a suitable location such that only a target portion including the ROI of the subject may be scanned.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, the processing engine 140 may include one or more additional modules. For example, the processing engine 140 may further include a storage module configured to store data generated by the above mentioned modules in the processing engine 140. In some embodiments, one or more modules of the processing engine 140 described above may be omitted. For example, the transmission module 440 may be omitted.

Figure 5:
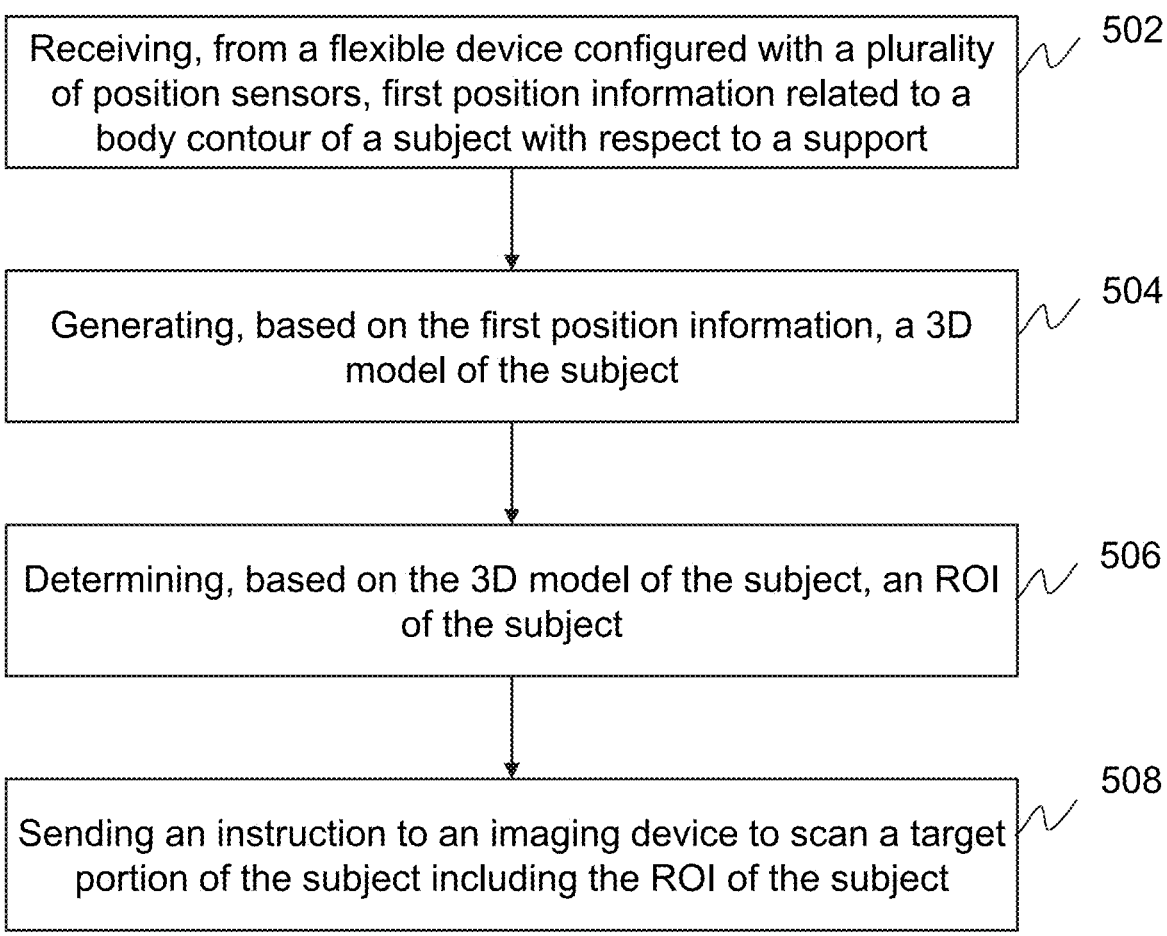
FIG. 5 is a flowchart illustrating an exemplary process for scanning a subject by an imaging device according to some embodiments of the present disclosure.

FIG. 5 is a flowchart illustrating an exemplary process for scanning a subject by an imaging device according to some embodiments of the present disclosure. In some embodiments, one or more operations of process 500 illustrated in FIG. 5 may be implemented in the imaging system 100 illustrated in FIG. 1. For example, at least a part of the process 500 illustrated in FIG. 5 may be stored in the storage device 150 in the form of instructions, and invoked and/or executed by the processing engine 140 (e.g., the processor 210 of the computing device 200 as illustrated in FIG. 2, the GPU 330 or CPU 340 of the mobile device 300 as illustrated in FIG. 3).

In 502, the acquisition module 410 may receive, from a flexible device configured with a plurality of position sensors, first position information related to a body contour of a subject with respect to a support. The flexible device may refer to a device that is capable of being bent or deformed to generate a shape as required. For example, the flexible device may be a wearable device that can be worn by the subject, or a blanket that can cover the subject. When being worn by or placed on the subject, the flexible device may be configured to conform to the body contour of the subject. The support may be configured to provide support for the subject. In some embodiments, the support may be a board, a mat, etc.

The subject may be biological or non-biological. Merely by way of example, the subject may include a patient, a man-made object, etc. As another example, the subject may include a specific portion, cells, tissues, organs or a whole body of a human or animal. For illustration purpose, a patient is taken as an example of the subject. The patient may lie on the support wearing the flexible device or be covered by the flexible device and the body of the patient may occupy a specific area on the support.

In some embodiments, the flexible device may be worn or placed on the body of the subject or a portion of the subject (collectively referred to as the subject herein). In some embodiments, the flexible device may be worn by or placed on the subject and cover the whole body of the subject. Additionally or alternatively, the flexible device may be worn by or placed on the subject and cover a portion of the subject. For example, the flexible device may cover front body surface of the subject (i.e., the portion of body surface not contacting the support) when the subject lies on the support. As another example, the flexible device may cover the body surface of the lower part of the subject (e.g., the legs of a patient). In some embodiments, the flexible device may include a plurality of sub-flexible devices configured to conform to different portions of the subject. Merely by way of example, the flexible device may include a plurality of sub-flexible devices configured for different parts of a patient's body (e.g., head, arm, leg). The sub-flexible devices may have the same or different sizes and configurations according to different situations.

When the flexible device is worn by or placed on the subject, the flexible device may be deformed to conform to the body contour of the subject. The flexible device may include a plurality of position sensors. The position sensors may be configured to collect first position information related to the body contour of the subject with respect to the support. In some embodiments, the first position information may include a distance measurement between each of the plurality of position sensors in the flexible device and the support. For example, the first position information may include a plurality of distance measurements, each of which indicates a distance between one of the plurality of position sensors and the support along the Y-axis as illustrated in FIG. 1. The position sensors may be close to the body surface of the subject when the flexible device is worn by or placed on the subject. Accordingly, the distance between a point on the body contour of the subject and the support may be represented by the distance between the position sensor corresponding to the point on the body contour of the subject and the support. The distance measurements between the plurality of position sensors and the support may then be regarded as distance measurements between the corresponding points on the body contour of the subject and the support, respectively.

In some embodiments, the position sensors of the flexible device may be any sensor that can measure distance. Exemplary position sensors may include a laser range finder, an infrared range finder, an ultrasonic range finder, a radar range finder, a microwave range finder, an electromagnetic range finder, or the like, or any combination thereof. In some embodiments, a position sensor may transmit and/or receive a signal (e.g., a microwave signal, an electromagnetic signal) that passes through the subject during distance measuring. For example, the position sensor may transmit the signal toward the support, and support a signal receiver mounted on the support may receive the signal. As another example, a signal transmitter may be mounted on the support and transmit the signal toward the position sensor of the flexible device. The position sensor and/or other components of the imaging system 100 (e.g., the processing engine 140, or the processor 210) may determine a distance measurement between the position sensor and the support based on the time of flight information of the signal. In some embodiments, the support may include a plurality of position sensors, and the signal transmitter and/or the signal receiver may be integrated into the position sensors of the support.

In some embodiments, the position sensors may determine a plurality of distance measurements along the Y-axis between the points on the subject and a reference substance. The reference substance may be, for example, a plane parallel to the support and locating on an opposite side of the subject with respect to the support. Based on the distance measurements between the points on the subject and the reference substance, the relative positions between different points on the subject, as well as the distance measurements between the points and the support may be determined.

In some embodiments, the position sensors of the flexible device may be arranged in an array. Each pair of adjacent position sensors may be connected to each other via a flexible connector. In some embodiments, the flexible device may include a plurality of units arranged in an array. Each of the plurality of units may include one or more position sensors. Each pair of adjacent units may be connected to each other via a flexible connector. A flexible connector may refer to a connector connecting two adjacent position sensors and/or units that is capable of being bent or deformed without breaking. Details regarding the configuration of the flexible device may be found elsewhere in the present disclosure (e.g., FIGS. 8A to 9 and the relevant descriptions thereof).

The subject may be supported by the support, which may provide a structural support for the subject. In some embodiments, the support may be the scanning table 114 of the imaging device 110. In some embodiments, the support may be configured with a plurality of detecting units to obtain information related to the subject. Exemplary detecting units may include pressure sensors, thermal sensors, position sensors, or the like, or any combination thereof. In some embodiments, the support may include a plurality of position sensors configured to collect first position information related the body contour of the subject with respect to the support. The position sensors of the support may be similar to that of the flexible device, and the descriptions thereof are not repeated.

In 504, the model generation module 420 may generate a 3D model of the subject based on the first position information. The first position information may include a plurality of distance measurements between points on the body contour of the subject and the support as described in connection with operation 502. The model generation module 420 may generate the 3D model of the subject based on the distance measurements between the points on the body contour and the support. In some embodiments, the 3D model may be generated based on a 3D reconstruction technique, a surface fitting technique, or any other suitable technique that can be used to generate a 3D model. Exemplary 3D reconstruction techniques may include an algorithm based on boundary contours, an algorithm based on non-uniform rational B-splines (NURBS), an algorithm based on a triangulation model, etc. Exemplary surface fitting techniques may include a least squares (LS) algorithm, a moving least squares algorithm (MLS), etc. In some embodiments, the 3D model may be generated based on a Stereo Lithographic (STL) model. The position information collected by the plurality of positions sensors in the flexible device worn by the subject may be denoted as distributed cloud points in a 3D space. Every three distributed cloud points may form a micro triangle grid or a micro triangle plane. The 3D model generated based on the STL model may include a plurality of micro triangle planes that form the body contour of the subject. In some embodiments, the model generation module 420 may further transmit the 3D model to a terminal 130 via the network 120 for display.

In some embodiments, the model generation module 420 may generate a 3D curved surface corresponding to the front body surface of the subject (i.e., the portion of body surface not contacting the subject when the subject lies on the support). The 3D curved surface may be directly used as the 3D model of the subject. In some embodiments, a plane or a curved surface may be used to represent the back portion of the surface and fit with the reconstructed 3D curved surface to generate the 3D model of the subject. In some embodiments, a planar body contour image of the subject on the support may be generated and combined with the reconstructed 3D curve surface to generate the 3D model. Details regarding the planar body contour image may be found elsewhere in the present disclosure (e.g., FIG. 8A and the relevant descriptions thereof).

In 506, the ROI determination module 430 may determine an ROI of the subject based on the 3D model of the subject.

As used herein, the "determining an ROI" may refer to determine a position of the ROI in the subject with respect to the imaging device 110. The ROI may be an entire body of the subject or a portion of the subject (e.g., one or more organs) depending on diagnostic needs. For example, the ROI may be an esophagus, a trachea, a bronchus, a stomach, a gallbladder, a small intestine, a colon, a bladder, a ureter, a uterus, a fallopian tube, or the like, or any combination thereof.

In some embodiments, the position of the ROI in the subject with respect to the imaging device 110 may be determined according the relative position of the ROI inside the subject and second position information of the subject with respect to the imaging device 110. The relative position of the ROI inside the subject may be determined based on the 3D model. The second position information of the subject with respect to the imaging device 110 may be determined based on an image of the subject indicating the position of the subject on the support, a spatial correlation between the ROI and a reference object located outside the subject (e.g., a marker installed on the scanning table 114), or the like, or any combination thereof. In some embodiments, at least part of the second position information may be determined based on the support. Details regarding the determination of an ROI may be found elsewhere in the present disclosure (e.g., FIG. 6 and the relevant descriptions thereof).

In 508, the transmission module 440 may send an instruction to the imaging device 110 to scan a target portion of the subject including the ROI of the subject.

The target portion of the subject may be a region including the ROI. For example, if the ROI corresponds to a heart of the subject, the target portion may be the chest of the subject including the entire heart, the lungs and a part of other tissues or vessels close to the heart. In some embodiments, the target portion to be scanned may be determined manually by an operator or automatically by the processing engine 140. For example, an operator may manually set the target portion on an image and/or the 3D model of the subject displayed on the GUI. As another example, the processing engine 140 may automatically set a target portion based on the position of the ROI with respect to the imaging device 110 and information related to a scanning protocol of the subject.

In some embodiments, the transmission module 440 may send an instruction to operate the imaging device 110 to adjust the position of the scanning table 114 to a suitable location such that the target portion of the subject may be scanned. The instructions may involve various parameters related to the movement of the scanning table 114. Exemplary parameters related to the movement of the scanning table 114 may include the distance of movement, the direction of movement, the speed of movement, or the like, or a combination thereof. As another example, the transmission module 440 may send an instruction to operate the imaging device 110 to adjust the position of other components of the imaging device 110, e.g., the radioactive scanning source 115, or other mechanical parts connected to the scanning table 114.

It should be noted that the above description regarding the process 500 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more operations may be added or omitted. For example, operation 506 may be divided into multiple operations which include determining the position of the ROI inside the subject and the position of subject with respect to the imaging device 110. In some embodiments, operation 508 may be omitted. In some embodiments, the instruction to scan the target portion may be inputted by a user (e.g., a doctor) via a terminal (e.g., the terminal 130).

Figure 6:
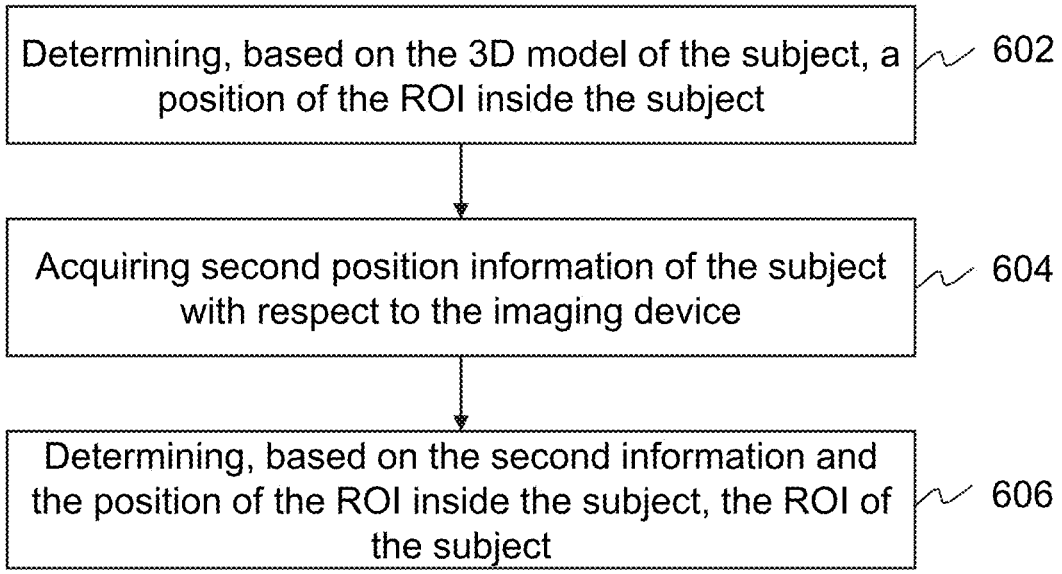
FIG. 6 is a flowchart illustrating an exemplary process for determining an ROI of a subject according to some embodiments of the present disclosure.

FIG. 6 is a flowchart illustrating an exemplary process for determining an ROI of a subject according to some embodiments of the present disclosure. In some embodiments, one or more operations of process 600 illustrated in FIG. 6 may be implemented in the imaging system 100 illustrated in FIG. 1. For example, at least a part of the process 600 illustrated in FIG. 6 may be stored in the storage device 150 in the form of instructions, and invoked and/or executed by the processing engine 140 (e.g., the processor 210 of the computing device 200 as illustrated in FIG. 2, the GPU 330 or CPU 340 of the mobile device 300 as illustrated in FIG. 3).

In 602, the ROI determination module 430 may determine a position of the ROI inside the subject based on the 3D model of the subject. In some embodiments, the position of the ROI inside the subject may be manually set by a user of the imaging system 100. Merely by way of example, the 3D model may be displayed on a terminal 130. The user may select a region in the 3D model, and the ROI determination module 430 may designate the selected region as the ROI in response to the user's selection. In some embodiments, after the user selects the region, a pre-scan may be performed on the selected region to generate a pre-scanned image of the selected region. The ROI determination module 430 may further determine the position of the ROI inside the subject based on the pre-scanned image.

In some embodiments, the ROI determination module 430 may determine the position of the ROI inside the subject based on information associated with thermal distribution of the subject. The temperatures of different organs in the subject may be different and lead to different levels of thermal radiations. The position of the ROI may be determined based on the information associated with thermal distribution of the subject. Details regarding the determination of the ROI based on information associated with thermal distribution of the subject may be found elsewhere in the present disclosure (e.g., FIG. 7A and the relevant descriptions thereof). In some embodiments, the ROI determination module 430 may determine the position of the ROI inside the subject based on physiological data and anatomical information related to the subject. Details regarding the determination of the ROI based on physiological data and anatomical information related to the subject may be found elsewhere in the present disclosure (e.g., FIG. 7B and the relevant descriptions thereof).

In 604, the ROI determination module 430 may acquire second position information of the subject respect to the imaging device 110.

In some embodiments, the second position information of the subject with respect to the imaging device 110 may be determined according to an image of the subject indicating a spatial correlation between the subject and the scanning table 114. For example, an image acquisition device (e.g., a camera) may be mounted on the gantry 111 of an imaging device 110 to record the position of the subject with respect to the scanning table 114. As another example, the support may be the scanning table 114 or be placed at a specific position on the scanning table 114. The support may include a plurality of pressure sensors configured to measure the pressure values generated by the subject on different parts of the support. The processing engine 140 may further generate a planar image of the body contour of the subject on the support based on the pressure values, which may further indicate the spatial correlation between the subject and the scanning table 114. In some embodiments, the position of the ROI in the subject with respect to the imaging device 110 may be determined according to the spatial correlation between the ROI and a reference object located outside the subject (e.g., a marker installed on the scanning table 114). Exemplary techniques for determining a position of a subject with respect to an imaging device 110 may be found in, for example, International Application No. PCT/CN2017/119896, entitled "SYSTEMS AND METHODS FOR PATIENT POSITIONING" filed on even date of the present application, the contents of which are hereby incorporated by reference.

In 606, the ROI determination module 430 may determine the ROI of the subject based on the position of the ROI inside the subject and the second position information of the subject with respect to the imaging device 110. After the position of the ROI inside the subject and the position of the subject with respect to the imaging device 110 are determined, the ROI determination module 430 may determine the position of the ROI with respect to the imaging device 110 accordingly.

Figure 7A:
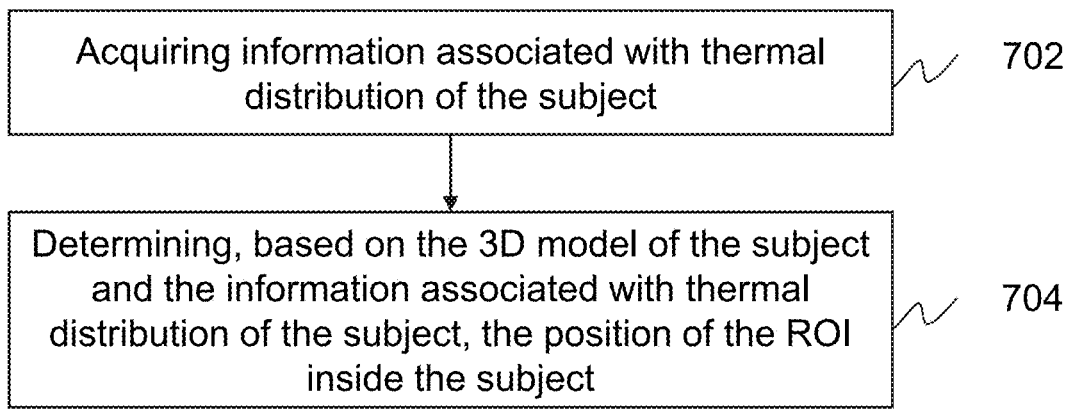
FIG. 7A is a flowchart illustrating an exemplary process for determining a position of an ROI inside a subject based on thermal distribution information according to some embodiments of the present disclosure.

FIG. 7A is a flowchart illustrating an exemplary process for determining a position of an ROI inside a subject based on thermal distribution information according to some embodiments of the present disclosure. In some embodiments, one or more operations of process 700A illustrated in FIG. 7A may be implemented in the imaging system 100 illustrated in FIG. 1. For example, at least a part of the process 700A illustrated in FIG. 7A may be stored in the storage device 150 in the form of instructions, and invoked and/or executed by the processing engine 140 (e.g., the processor 210 of the computing device 200 as illustrated in FIG. 2, the GPU 330 or CPU 340 of the mobile device 300 as illustrated in FIG. 3).

In 702, the ROI determination module 430 may acquire information associated with thermal distribution of the subject.

In some embodiments, the information associated with the thermal distribution of the subject may be acquired by using an infrared thermography technique. An object with a temperature above absolute zero may emit infrared radiations. The amount of infrared radiations emitted by the object may increase with the temperature of the object. Different organs or regions of a human/animal body may have different temperatures, and thus may emit different amounts of infrared radiations. In some embodiments, the flexible device and/or the support may include a plurality of thermal sensors. The plurality of thermal sensors may measure infrared radiations emitted from different portions of the subject. The processing engine 140 may further generate an infrared thermal distribution image (also referred to as an infrared thermogram) based on the infrared radiations measured by the thermal sensors. The thermal distribution image may illustrate the thermal distribution of the subject by using different colors to represent regions with different temperatures.

In some embodiments, information associated with the thermal distribution of the subject may be acquired by a thermal imaging device, such as an infrared imaging device. The thermal imaging device may detect thermal radiations from the subject, and determine the heat distribution on the surface of the subject based on the thermal radiations. The thermal imaging device may further employ a thermoelectric analogy technique to determine one or more heat sources (e.g., the one or more organs) of the subject based on the heat distribution on the surface of the subject. For example, the thermal imaging device may determine the thermal radiation level, the depth, the position, and/or the shape of each of the one or more heat sources (e.g., the one or more organs) beneath the surface of the subject. In some embodiments, the thermal imaging device may generate an infrared thermal distribution image of the subject based on the detected thermal radiations.

In 704, the ROI determination module 430 may determine the position of the ROI inside the subject based on the 3D model of the subject and the information associated with the thermal distribution of the subject. For example, the infrared thermal distribution image of the subject may indicate the locations of different organs or tissues with different temperatures. The ROI determination module 430 may determine the position of the ROI with respect to the 3D model of the subject based on the infrared thermal distribution image.

Figure 7B:
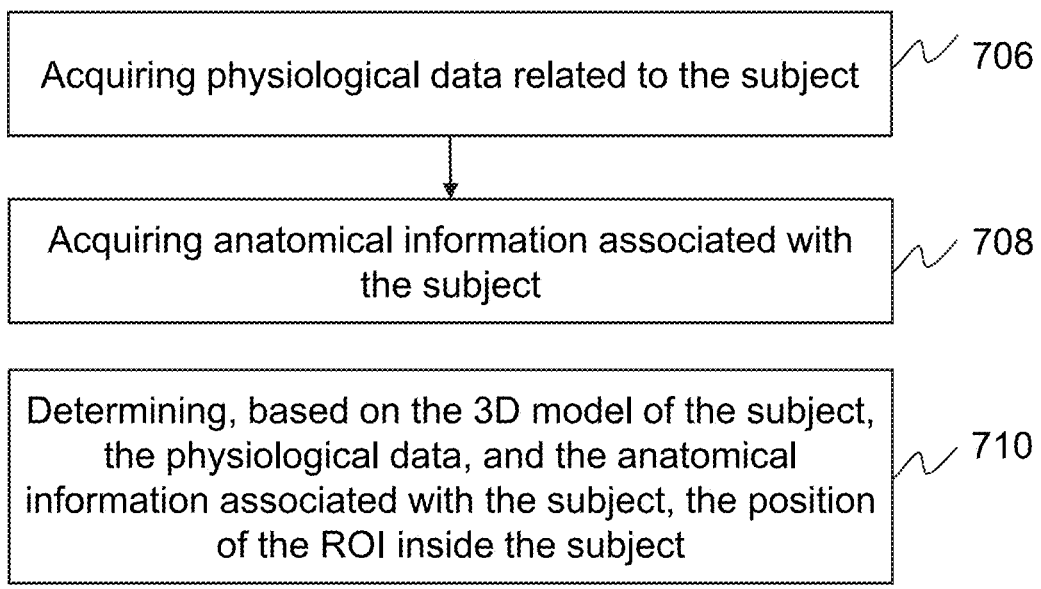
FIG. 7B is a flowchart illustrating an exemplary process for determining a position of an ROI inside a subject based on physiological data and anatomical information according to some embodiments of the present disclosure.

FIG. 7B is a flowchart illustrating an exemplary process for determining a position of an ROI inside a subject based on physiological data and anatomical information according to some embodiments of the present disclosure. In some embodiments, one or more operations of process 700B illustrated in FIG. 7B may be implemented in the imaging system 100 illustrated in FIG. 1. For example, at least a part of the process 700B illustrated in FIG. 7B may be stored in the storage device 150 in the form of instructions, and invoked and/or executed by the processing engine 140 (e.g., the processor 210 of the computing device 200 as illustrated in FIG. 2, the GPU 330 or CPU 340 of the mobile device 300 as illustrated in FIG. 3).

In 706, the ROI determination module 430 may acquire physiological data related to the subject.

The physiological data may include a weight, a height, a body mass index (BMI), a body fat percentage, or the like, or any combination thereof. In some embodiments, the physiological data may be historical data retrieved from a storage device (e.g., the storage device 150). Additionally or alternatively, the physiological data may be measured before or during the medical examination using a measurement instrument of physiological data.

In some embodiments, at least part of the physiological data may be acquired from the support. Merely by way of example, the support may include a plurality of pressure sensors configured to measure pressure values of the subject. The weight of the subject may be determined based on the total amount of pressure values detected by the pressure sensors. As another example, when the pressure sensors are arranged in a point array, the height of the subject may be determined based on the locations of the pressure sensors on the support. The BMI may be calculated by dividing the weight by the square of the height.

In some embodiments, at least part of the physiological data may be determined based on the 3D model. For example, the ROI determination module 430 may determine physiological data related to the subject based on the 3D model. Exemplary physiological data determined based on the 3D model may include a height, a volume, a thickness, a width of the subject or a portion thereof (e.g., a leg).

In 708, the ROI determination module 430 may acquire anatomical information associated with the subject.

The anatomical information associated with the subject may include any information indicating the physiological structure of the subject. For example, the anatomical information may indicate the position, the shape, the volume, the size of one or more organs and/or tissues of the subject. In some embodiments, the anatomical information may be acquired according to history data related the subject. For example, the anatomical information may be a historical medical image (e.g., a CT image, an MRI image) of the subject including anatomical information. Additionally or alternatively, the anatomical information may be acquired from anatomical information of reference samples relate to the subject. The locations of different organs (e.g., a heart, a lung, etc.) and tissue (e.g., a bone, an aorta, etc.) may be similar between individuals, and may be affected by physiological data such as the weight, the height, the body type, etc. A reference sample related to the subject may refer to a sample (e.g., a person) having a similar characteristic to the subject (e.g., a similar height or weight). For example, the ROI determination module 430 may acquire anatomical information associated with the subject according to anatomical information (e.g., medical images) of other persons having a similar characteristic to the subject (e.g., a similar height or weight).

In some embodiments, the anatomical information associated with the subject may be stored in a storage device (e.g., the storage device 150). The ROI determination module 430 may access the storage device and retrieve the anatomical information associated with the subject. Additionally or alternatively, the ROI determination module 430 may obtain the anatomical information associated with the subject from external sources (e.g., a database of a hospital or medical institution) via the network 120.

In 710, the ROI determination module 430 may determine the position of the ROI inside the subject based on the 3D model of the subject, the physiological data, and anatomical information associated with the subject. In some embodiments, the ROI determination module 430 may determine the position of the ROI with respect to the 3D model of the subject based the physiological data, and the anatomical information according to a morphological method.

It should be noted that the above description regarding the process 700A and process 700B is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more operations may be added or omitted. For example, the operation 706 may be omitted. The ROI determination module 430 may determine the position of the ROI inside the subject based on the 3D model and the anatomical information associated with the subject. Merely by way of example, the position of the ROI inside the subject may be determined based on the 3D model and a historical medical image of the subject or historical medical images of other samples. In some embodiments, the ROI determination module 430 may determine the position of the ROI inside the subject based on the thermal distribution information and/or the anatomical information without the 3D model. For example, the ROI determination module 430 may determine the position of the ROI inside the subject directly based on a thermal distribution image of the subject.

Figure 8A:
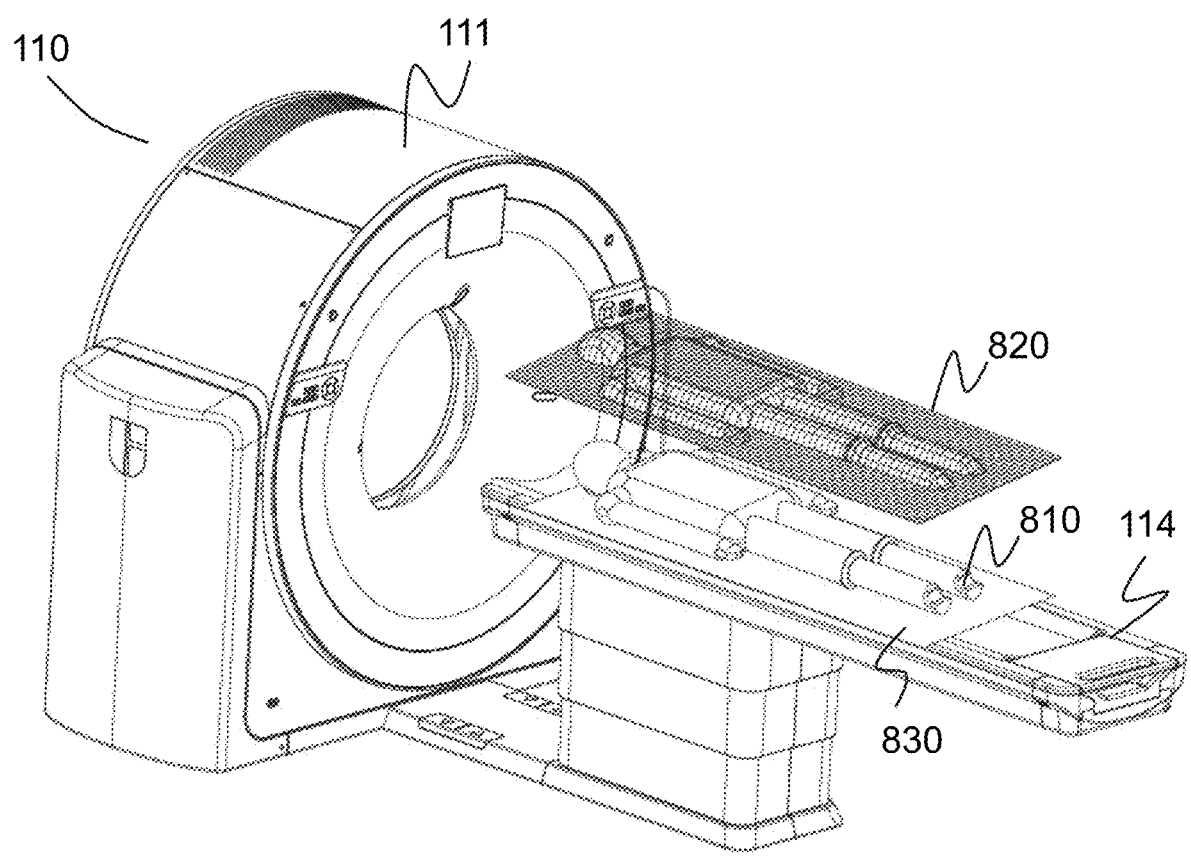
FIGS. 8A to 8C are schematic diagrams illustrating an exemplary imaging system according to some embodiments of the present disclosure.
Figure 8B:
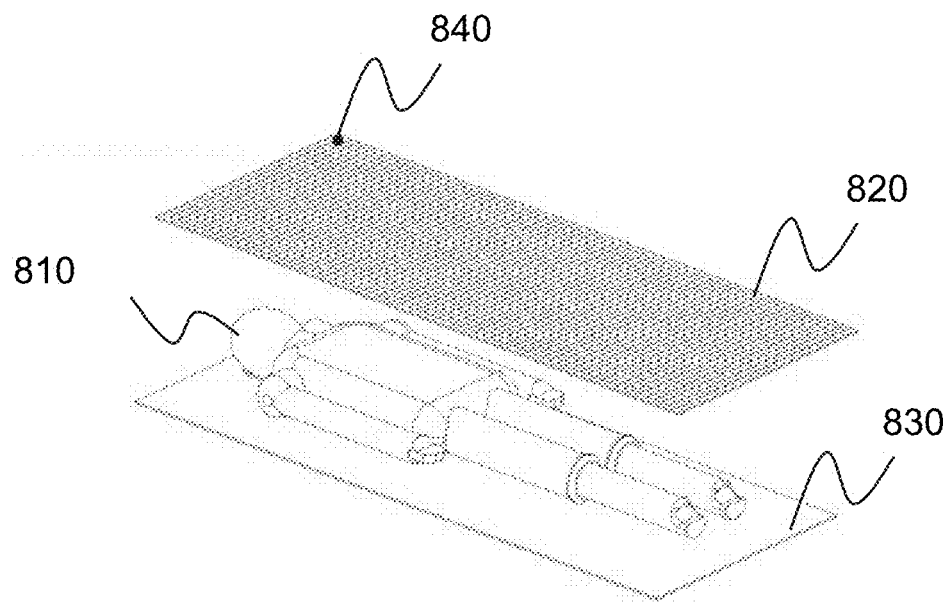
Figure 8C:
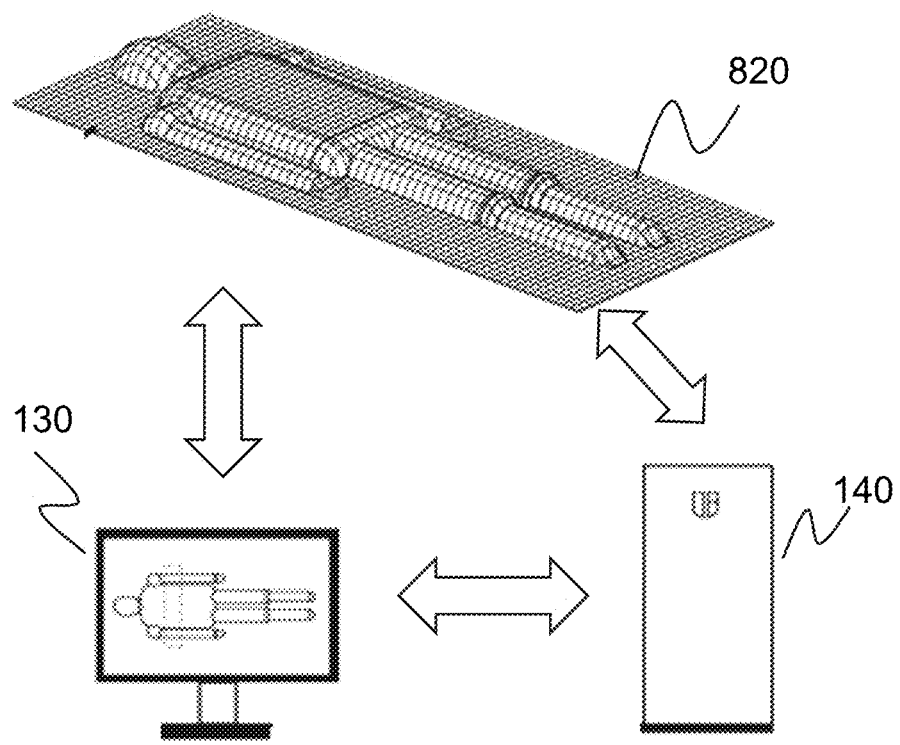

FIGS. 8A to 8C are schematic diagrams illustrating an exemplary imaging system 800 according to some embodiments of the present disclosure. As shown, the imaging system 800 may include an imaging device 110, a flexible device 820, and a support 830. The imaging device 110 may include a gantry 111 and a scanning table 114. In some embodiments, the imaging system 800 may further include one or more same or similar components as the imaging system 100.

As shown in FIG. 8A, a subject 810 may wear or be covered by a flexible device 820 and lie on the support 830. The support 830 may be placed on the scanning table 114. In some embodiments, the scanning table 114 may further include a table top and a sliding rail. During a scan, the imaging device 110 may adjust the position of the subject 810 by moving the table top through the sliding rail.

The flexible device 820 may conform to the body contour of the subject 810 and be used to determine the body contour of the subject 810. The flexible device 820 may include a plurality of position sensors configured to collect first position information related to the body contour of the subject 810 with respect to the support 830. In some embodiment, the flexible device 820 may be removed from the subject before a medical scan.

The support 830 may provide a structural support for the subject 810. In some embodiments, the support 830 may be configured with a plurality of sensors to collect information related to the subject 810. Exemplary sensors may include pressure sensors, thermal sensors, position sensors, or the like, or any combination thereof. Exemplary information collected by the support 830 may include weight, height, a plurality of distance measurements between the body contour of the subject 810 and the support 830, position information of the subject 810 with respect to the support 830, or the like, or any combination thereof.

In some embodiments, a plurality of pressure sensors may be arranged on the support 830 to detect pressure values generated by the subject 810. The processing engine 140 may generate a planar body contour image of the subject 810 on the support 830 based on the pressure values. The planar body contour image of the subject 810 on the support 830 may indicate the position information of the subject 810 with respect to the support 830. In some embodiments, the support 830 may be the scanning table 114 or be placed at a specific position on the scanning table 114. The position information of the subject 810 with respect to the scanning table 114 may then be determined based on the position information of the subject 810 with respect to the support 830.

In some embodiments, the planar body contour image of the subject 810 on the support 830 may be combined with the first position information including a plurality of distance measurements between the body contour and the support 830 to generate the 3D model of the subject 810. For example, a 3D curved surface corresponding to the front body surface of the subject (i.e., the portion of body surface not contacting the subject when the subject lies on a scanning table) may be generated based on the first position information. The planar body contour image may be used to represent the back portion of the subject and fit with the 3D curved surface to generate the 3D model of the subject.

In some embodiments, as illustrated in FIG. 8B, the flexible device 820 may include a plurality of units 840. The plurality of units 840 may be arranged, for example, in a dot array. Each of the plurality of units 840 may include one or more sensors, for example, position sensors, thermal sensors, etc. A unit 840 may be connected to one or more units 840 via one or more flexible connectors. Thus the flexible device 820 may be deformed to conform to the body shape of the subject 810. In some embodiments, a unit 840 may include one or more protective layers covering the one or more sensors of the unit 840. Detailed information regarding a structure of the flexible device 820 may be found in FIG. 9 and the descriptions thereof.

In some embodiments, the imaging system 800 may include one or more same or similar components as the imaging system 100, such as one or more terminals 130 and a processing engine 140. The flexible device 820 may be connected to and/or communicated with one or more other components of the imaging system 800 via a wired connection or a wireless connection (e.g., a network), or a combination thereof. For example, as illustrated in FIG. 8C, the flexible device 820 may be may be connected to and/or communicated with the terminal 130 and the processing engine 140. The flexible device 820 may transmit detected information associated with the subject (e.g., distance information between the body contour of the subject 810 and the support 830, infrared radiations emitted by the subject 810, etc.) to the processing engine 140. The processing engine 140 may process the information received from the flexible device 820. For example, the processing engine 140 may generate a 3D model and/or an infrared thermal distribution image of the subject 810.

In some embodiments, the flexible device 820 and/or the processing engine 140 may further transmit the information or the processed information to the terminal 130 for display. An operator may view the information and/or the processed information via the interface of the terminal 130. Additionally or alternatively, the operator may also input data and/or instructions to the processing engine 140 and/or the flexible device 820 via the terminal 130. For example, the operator may instruct the flexible device 820 to collect information related to the subject 810. As another example, the operator may instruct the processing engine 140 to generate the 3D model of the subject 810 based on the information collected by the flexible device 820.

In some embodiments, the support 830 may also be connected to and/or communicated with one or more other components of the imaging system 800. The connection between the support 830 and the other components may be similar to that of the flexible device 820, and the descriptions thereof are not repeated.

Figure 9:
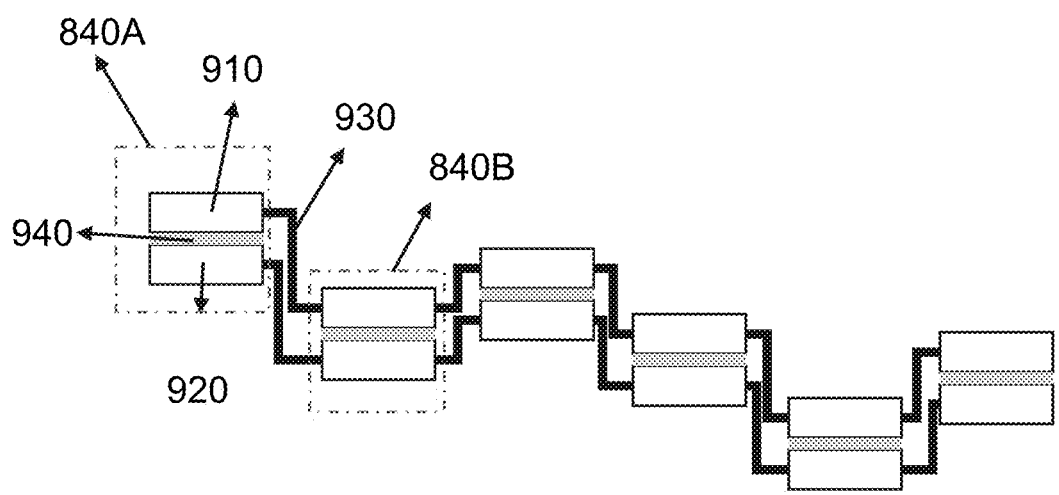
FIG. 9 is a schematic diagram illustrating an exemplary flexible device according to some embodiments of the present disclosure.

FIG. 9 is a schematic diagram illustrating an exemplary flexible device 820 according to some embodiments of the present disclosure.

The flexible device 820 may include a plurality of units arranged in a dot array. Each unit may include one or more position sensors. Each pair of adjacent units of the plurality of units may be connected to each other via a flexible connector. In some embodiments, different units of the flexible device 820 may have a same or different configurations. For example, each unit of the flexible device 820 may have the same size. As another example, different units may have different sizes and different numbers of position sensors configured with respect to different portions of the subject. In some embodiments, the flexible device 820 may be detachable and/or collapsible. For example, one or more flexible connectors of the flexible device 820 may be opened or removed, and the flexible device 820 may be disassembled to a plurality of sub-parts.

As illustrated in FIG. 9, the flexible device 820 may include a plurality of units. For illustration purposes, the configuration and arrangement of a unit 840A and a unit 840B are described as an example. The unit 840A and the unit 840B may be connected to each other by a flexible connector 930. The flexible connector 930 may be capable of being bent or deformed without breaking. The relative position between the unit 840A and the unit 840B may change via the flexible connector 930 to conform to the body contour of the subject. For example, the angel between the unit 840A and the unit 840B may change so that the flexible device 820 may better fit the body contour of the subject. In some embodiments, the unit 840A and the unit 840B may be detachable by, such as opening or removing the flexible connector 930. In some embodiments, the flexible connector 930 may include a plurality of flexible fibers. The flexible connector 930 may be made of any flexible material, such as a composite of fiber and soft rubber, a biology fiber material, or the like, or any combination thereof.

The unit 840A may include one or more sensors 940, a first layer 910, and a second layer 920. The unit 840A may also include one or more thermal sensors (not shown). The position sensor(s) 940 may be sandwiched between the first layer 910 and the second layer 920 as illustrated in FIG. 9. The first layer 910 and the second layer 920 may provide structural support and protection for the sensor(s) 940, and make the flexible device 820 more comfortable to subject 810. In some embodiments, the first layer 910 and the second layer 920 may be made of materials such as an artificial fiber, a plant fiber, etc. The constitution of the first layer 910 and the second layer 920 may or may not be the same. The unit 840B may have the same or similar configuration as the unit 840A, and the descriptions thereof are not repeated.

It should be noted that the examples illustrated in FIG. 8A to FIG. 9 and the above descriptions thereof are merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the flexible device 820 may be configured in any shape and size. As another example, the position sensor(s) 940 of the unit 840A may be covered by one of the first layer 910 and the second layer 920. As yet another example, the position sensor(s) 940 may be covered by more than two layers on the upper side, the bottom side, or both sides.

Figure 10:
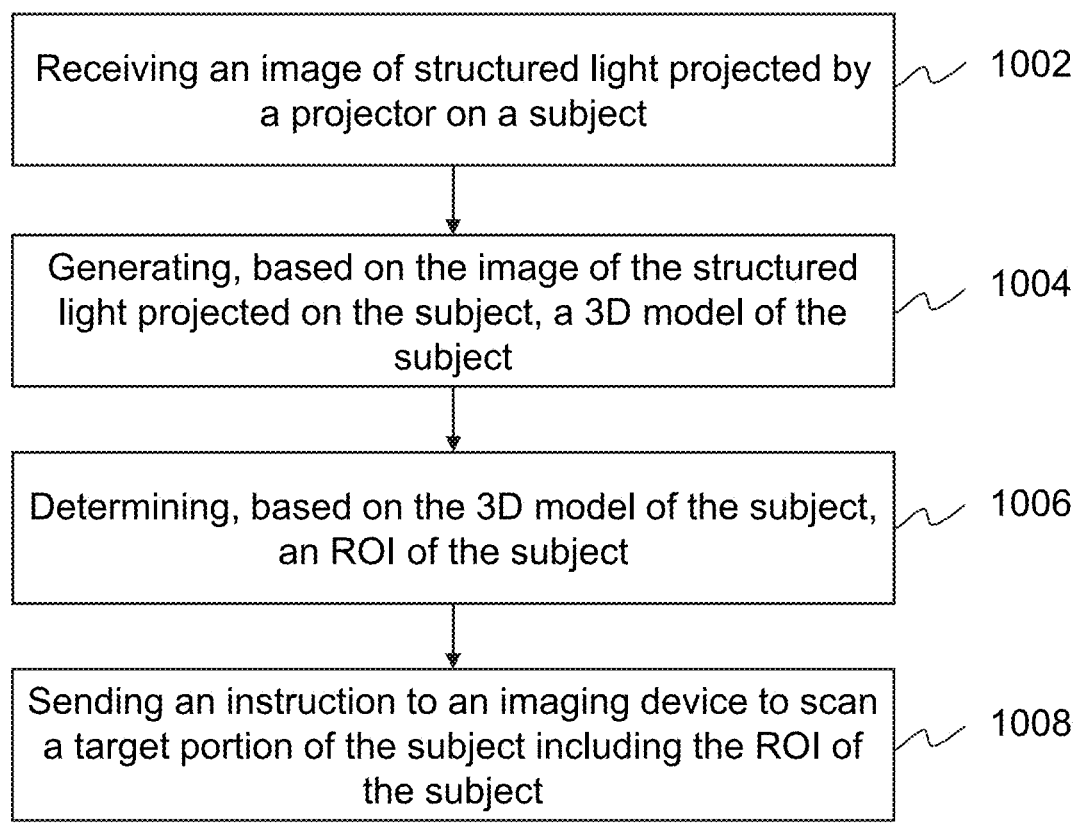
FIG. 10 is a flowchart illustrating an exemplary process for scanning a subject by an imaging device according to some embodiments of the present disclosure.

FIG. 10 is a flowchart illustrating an exemplary process for scanning a subject by an imaging device according to some embodiments of the present disclosure. In some embodiments, one or more operations of process 1000 illustrated in FIG. 10 may be implemented in the imaging system 100 illustrated in FIG. 1. For example, at least a part of the process 1000 illustrated in FIG. 10 may be stored in the storage device 150 in the form of instructions, and invoked and/or executed by the processing engine 140 (e.g., the processor 210 of the computing device 200 as illustrated in FIG. 2, the GPU 330 or CPU 340 of the mobile device 300 as illustrated in FIG. 3).

In 1002, the acquisition module 410 may receive an image of structured light projected by a projector on a subject.

The structured light may refer to light that has a certain pattern projected to the subject. The structured light may include a structured light spot, a structured light stripe, a structured light grid, or the like. The structured light may be visible or invisible. The visible structured light may have a visually distinguishable color, for example, red, green, etc. Exemplary invisible structured light may include infrared light.

The structured light may be projected on the subject by a projector. The image of the structured light on the subject may be captured by an imaging acquisition device from other perspectives than the projector. The imaging acquisition device may be and/or include any suitable device capable of acquiring image data under the structured light. Exemplary imaging acquisition devices may include a digital camera, a video recorder, a mobile phone, an infrared camera, or the like. When the structured light is projected on the subject with a shaped body surface, the structured light may be distorted due to the shaped body surface. The image of the structured light projected on the subject may be used for a geometric reconstruction of the body surface shape of subject.

In some embodiments, the projector may project the structured light on the subject from different perspectives. For example, the projector may project the structured light on the subject at a plurality of positions. The imaging acquisition device may capture a plurality of images of the structured light projected on the subject when the projector projects the structured light on the subject at different positions. Additionally or alternatively, the imaging acquisition device may capture a plurality of images of the structured light projected on the subject from different perspectives, or a plurality of imaging acquisition devices may be configured at different positions with respect to the subject to capture a plurality of images from different perspectives.

In some embodiments, the structured light projected by the projector may cover the entire body of the subject. The projector may be configured at a fixed positon to project the structured light on the subject. Alternatively, the structured light may cover a portion of the body of the subject. The projector may be moved to different positions to project the subject. Details regarding the movable projector may be found elsewhere in the present disclosure (e.g., FIG. 12 and the relevant descriptions thereof).

In 1004, the model generation module 420 may generate a 3D model of the subject based on the image(s) of the structured light projected on the subject.

In some embodiments, the structured light projected on the subject may be considered as a plurality of light spots. The model generation module 420 may determine a coordinate of a light spot based on the image(s) of the structured light projected on the subject and a geometric relationship among the projector, the imaging acquisition device and the light spot. A light spot with a determined coordinate may be considered as a point on the body contour of the subject. The model generation module 420 may generate a 3D curved surface of the body contour of the subject based on a plurality of points with determined coordinates according to a 3D reconstruction algorithm. Exemplary 3D reconstruction algorithms may include an algorithm based on boundary contours, an algorithm based on non-uniform rational B-splines (NURBS), an algorithm based on a triangulation model, etc.

In some embodiments, the model generation module 420 may generate the 3D model based on a phase method. For example, the model generation module 420 may determine information related to phase shifts based on the image of the structured light projected on the subject. The model determination module 420 may then determine depth information related to the body contour of the subject based on the information related to phase shifts, and use a surface fitting algorithm to generate the 3D curved surface based on the depth information. Exemplary surface fitting algorithm may include a least squares (LS) algorithm, a moving least squares algorithm (MLS), etc. It should be noted that the above descriptions are merely provided for the purposes of illustration. The model generation module 420 may adopt any other suitable technique to generate the 3D model based on the image of the structured light.

In some embodiments, the model generation module 420 may generate a 3D curved surface corresponding to the front body surface of the subject (i.e., the portion of body surface not contacting the subject when the subject lies on a scanning table). The 3D curved surface may be directly used as the 3D model of the subject. In some embodiments, a plane or a curved surface may be used to represent the back portion of the surface and fit with the reconstructed 3D curved surface to generate the 3D model of the subject. In some embodiments, a planar body contour image of the subject on a support (e.g., the support 830) or a scanning table 114 may be generated and combined with the reconstructed 3D curve surface to generate the 3D model. Details regarding the planar body contour image may be found elsewhere in the present disclosure (e.g., FIG. 8A and the relevant descriptions thereof).

In 1006, the ROI determination module 430 may determine an ROI of the subject based on the 3D model of the subject. In some embodiments, the ROI determination module 430 may determine the position of the ROI with respect to the imaging device 110 based on the position of the ROI inside the subject and second position information related to the subject with respect to the imaging device 110.

In 1008, the transmission module 440 may send an instruction to an imaging device to scan a target portion of the subject including the ROI of the subject. In some embodiments, the target portion of the subject may be a region including the ROI. The transmission module 440 may send an instruction to operate the imaging device 110 to adjust the position of the scanning table 114 to a suitable location such that only the target portion of the subject may be scanned.

Operations 1006 and 1008 may be performed in a similar manner to operations 506 and 508 respectively, and the descriptions thereof are not repeated here. In some embodiments, operation 1008 may be omitted. In some embodiments, the instruction to scan the target portion may be inputted by a user (e.g., a doctor) via a terminal (e.g., the terminal 130).

FIG. 11 is a flowchart illustrating an exemplary process for scanning a subject by an imaging device according to some embodiments of the present disclosure. In some embodiments, one or more operations of process 1100 illustrated in FIG. 11 for scanning a subject may be implemented in the imaging system 100 illustrated in FIG. 1. For example, at least a part of the process 1100 illustrated in FIG. 11 may be stored in the storage device 150 in the form of instructions, and invoked and/or executed by the processing engine 140 (e.g., the processor 210 of the computing device 200 as illustrated in FIG. 2, the GPU 330 or CPU 340 of the mobile device 300 as illustrated in FIG. 3).

In 1102, the acquisition module 410 may receive distance information from a body contour of a subject to a light pulse generator. The distance information may be determined based on time of flight (TOF) information associated with light pulses emitted by the light pulse generator toward the subject.

In some embodiments, a light pulse generator may be configured to emit light pulses continuously on the body surface of the subject. The light pulse generator may be a laser tube, a light emitting diode (LED), a laser diode, or the like. In some embodiments, the light pulses emitted by the light pulse generator may have a specified characteristic (e.g., wavelength, pulse repetition rate (frequency), pulse width). For example, the frequency of the light pulses emitted by the light pulse generator may be equal to or greater than 100 MHz. The characteristics of the light pulses emitted by the light pulse generator may be default settings of the imaging system 100 or be set manually by a user via, such as a terminal 130. In some embodiments, the light pulse generator may be moving to emit light pulses on a desired region of the body surface of the subject, for example, to the entire body surface of the subject.

The light pulses may be reflected by the body surface of the subject and detected by a light pulse sensor. The light pulse sensor may be able to detect light pulse with the same or substantially same characteristic as that emitted by the light pulse generator. In some embodiments, a plurality of light pulse sensors may be configured detect reflected light pulses. The TOF information associated with each of the light pulse(s) may be collected and be used to determine the distance between the body contour and the light pulse. The TOF information related to a light pulse may refer to the time period between a time point when the light pulse is emitted from the light pulse generator and a time point when the reflected light pulse of the light pulse is detected by a light pulse sensor. In some embodiments, the TOF information may be recorded by a timer or be determined by, such as the processing engine 140, or the processor 210 based on a phase-shift technique.

The distance information from the body contour to the light pulse generator may then be determined based on the TOF information and the velocity of light. The distance information may include distance measurements between the points on the body contour of the subject and the light pulse generator. In some embodiments, the distance information from the body contour of the subject to the light pulse generator may be determined by one or more components in the imaging system 100, such as the processing engine 140 and transmitted to a storage device (e.g., the storage device 150) for storage. The acquisition module 410 may access and retrieve the distance information from the storage device.

In 1104, the model generation module 420 may generate a 3D model of the subject based on the distance information. In some embodiments, the model generation module 420 may obtain the location information (e.g., the coordinates) of the light pulse generator and the light pulse sensor that detects the light pulse. The location information (e.g., the coordinates) of one or more points on the body surface that reflect the light pulse may be determined based on the distance information and the corresponding coordinates of the light pulse generator and the light pulse sensor. The 3D model of the subject may be generated using similar methods described in operation 1004.

In 1106, the ROI determination module 430 may determine an ROI of the subject based on the 3D model of the subject.

In 1108, the transmission module 440 may send instruction to an imaging device to scan a target portion of the subject including the ROI of the subject.

Operations 1106 and 1108 may be performed in a similar manner to operations 506 and 508 respectively, and the descriptions thereof are not repeated here. In some embodiments, operation 1108 may be omitted. In some embodiments, the instruction to scan the target portion may be inputted by a user (e.g., a doctor) via a terminal (e.g., the terminal 130).

FIG. 12 is a schematic diagram illustrating an exemplary imaging system 1200 according to some embodiments of the present disclosure. In some embodiments, at least part of the process 500, at least part of the process 1000, and/or at least part of the process 1100 may be implemented on the imaging system 1200.

As illustrated in FIG. 12, the imaging system 1200 may include one or more same or similar components as the imaging system 100, such as the imaging device 110, a terminal 130, and a processing engine 140. The imaging device 110 may include an information acquisition component 1210. The information acquisition component 1210 may be configured to acquire information of a subject. For example, the information acquisition component 1210 may include a projector configured to project structured light on the subject. A camera may be configured to capture an image of the structured light projected on the subject, and the image may be used to generate the 3D model of the subject as described in connection with FIG. 10.

As another example, the information acquisition component 1210 may include a light pulse generator and/or a light pulse sensor. TOF information associated with light pulses emitted by the light pulse generator on the subject may be used to generate the 3D model of the subject as described in connection with FIG. 11. As yet another example, the information acquisition component 1210 may include or be an imaging acquisition device (e.g., a camera) configured to acquire one or more images of the subject. In some embodiments, the information acquisition component 1210 may be a camera capturing an image including position information of the subject with respect to the imaging device 110, and/or an image of structured light projected on the subject. In some embodiments, the information acquisition component 1210 may be an infrared camera configured to collect information associated with the thermal distribution of the subject.

In some embodiments, the information acquisition component 1210 may move to different positions to acquire information regarding the subject from different perspectives. For example, the information acquisition component 1210 may move from the start location to the end location as illustrated in FIG. 12. In some embodiments, the information acquisition component 1210 may move in different directions, for example, along the X axis, the Y axis, or the Z axis as illustrated in FIG. 1. The movement of the information acquisition component 1210 may be controlled by a user manually or by the processing engine 140 automatically.

The information acquisition component 1210 may be connected to and/or communicated with one or more other components of the imaging system 1200 via a wired connection or a wireless connection (e.g., a network), or a combination thereof. For example, as illustrated in FIG. 12, the information acquisition component 1210 may be connected to and/or communicated with the terminal 130 and the processing engine 140. The connection and/or communication between the information acquisition component 1210, the terminal 130, and/or the processing engine 140 may be similar to that between the flexible device 820, the terminal 130, and/or the processing engine 140, and the descriptions thereof are not repeated.

FIGS. 13A to 13E are schematic diagrams illustrating an exemplary imaging device 1300 according to some embodiments of the present disclosure. In some embodiments, the imaging device 1300 may be an exemplary embodiment of the imaging device 110.

The imaging device 1300 may include an information acquisition component 1210 as described in connection with FIG. 12. The information acquisition component 1210 may be configured to collection information with respect to the subject to be scanned. The information acquisition component 1210 may include, for example, a projector, an image acquisition device (e.g., a digital camera, an infrared camera), a light pulse generator, a light pulse sensor, or the like, or any combination thereof.

Figure 13A:
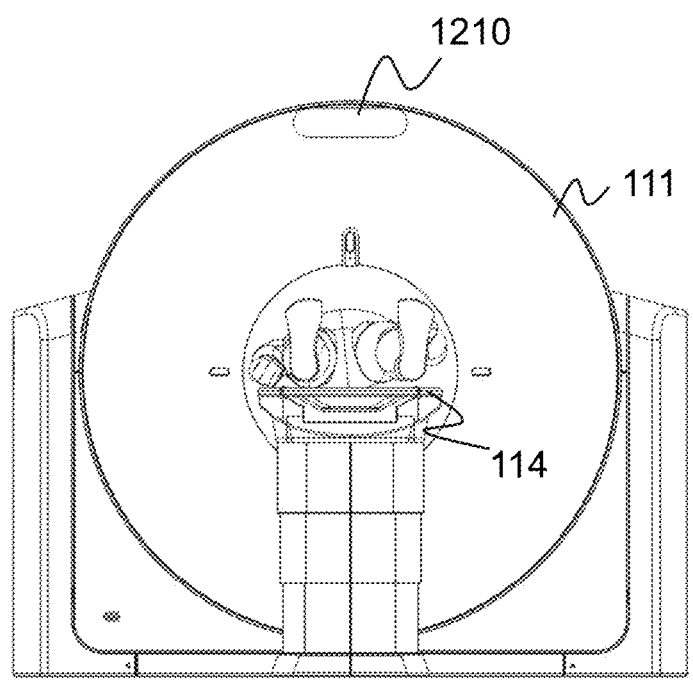
FIGS. 13A to 13E are schematic diagrams illustrating an exemplary imaging device according to some embodiments of the present disclosure.

The information acquisition component 1210 may be mounted on the gantry 111. The position and/or the configuration of the information acquisition component 1210 may be adjusted according to different situations by, for example, a user, the processing engine 140, or the like, or any combination thereof. For example, as illustrated in FIG. 13A, the information acquisition component 1210 may be retracted in the gantry 111 or a container mounted on the gantry 111 when not in use. This may provide protection for the information acquisition component 1210 against dust and provide a concise appearance for the imaging device 1300. When in use, the information acquisition component 1210 may be extended from the gantry 111 or the container to acquire information related to a portion of the subject or the entire subject.

Figure 13B:
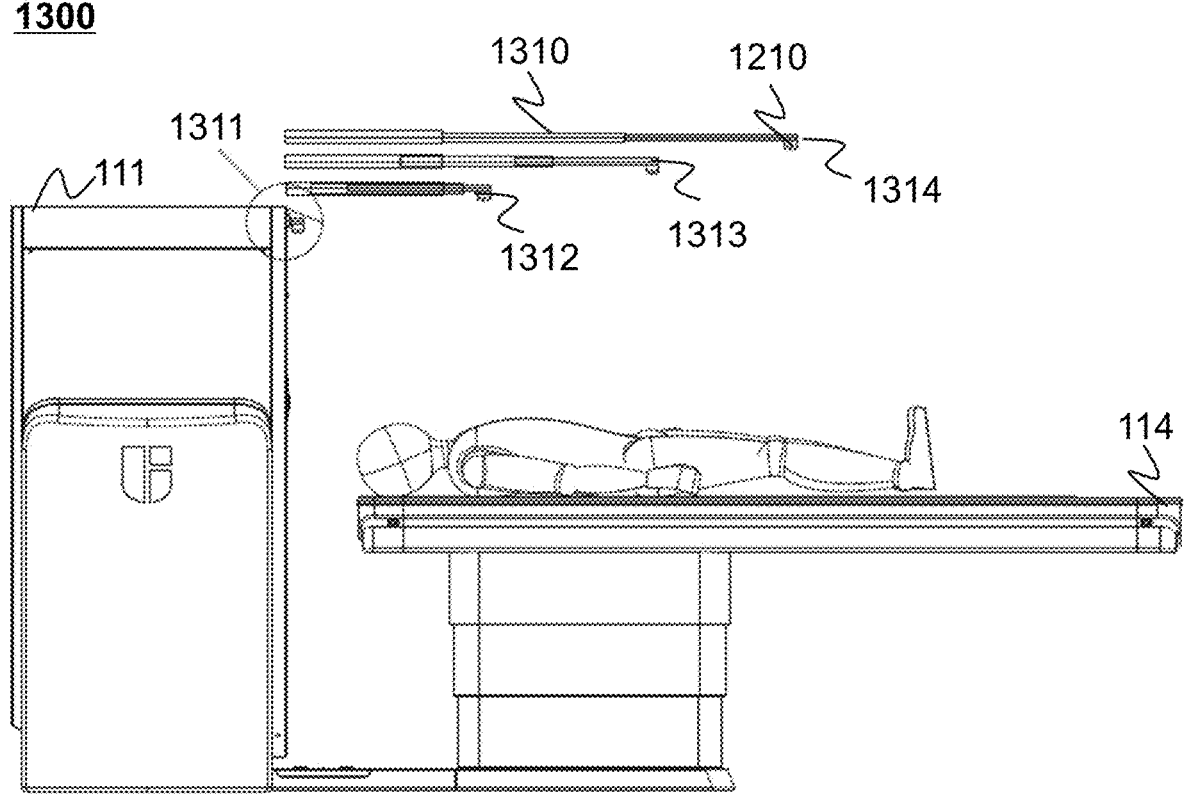

In some embodiments, as illustrated in FIG. 13B, the position of the information acquisition component 1210 may be controlled via an extendable pole 1310. The length of the extendable pole 1310 may be adjusted, such that the information acquisition component 1210 may acquire information related to the subject from different views. For example, the information acquisition component 1210 may collect information at different positions 1311, 1312, 1313, and 1314 when the extendable pole 1310 is at different extension lengths. The extendable pole 1310 is about to extend from the gantry 111 at the position 1311, and is fully extended at the position 1314. In some embodiments, during the movement driven by the extendable pole 1310, the information acquisition component 1210 may continuously or periodically acquire information related to the subject. For example, the information acquisition component 1210 may continuously capture images of the subject when it moves from the position 1311 to the position 1314.

Figure 13C:
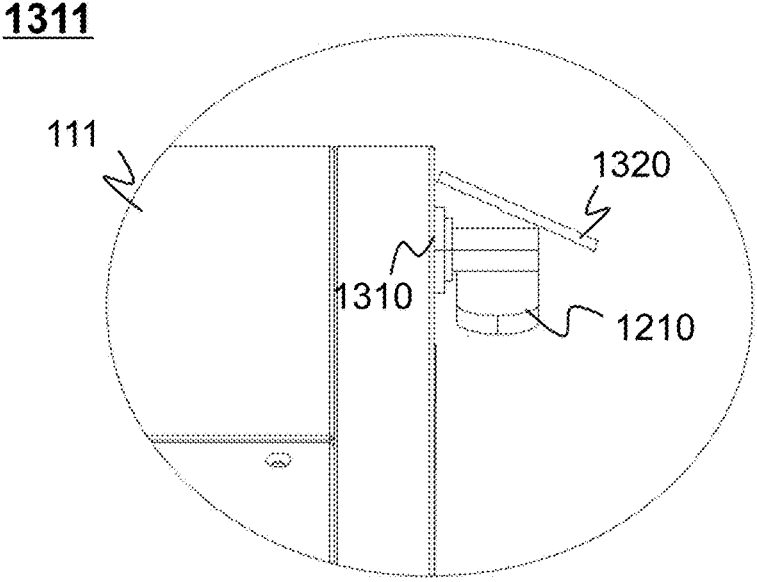

FIG. 13C illustrates an enlarged view of the information acquisition component 1210 at the position 1311. In some embodiments, the imaging device 1300 may further include a lid 1320. The lid 1320 may be configured to cover the information acquisition component 1210 when it is at a fully retracted position inside the gantry 111 or the container mounted on the gantry 111 as illustrated in FIG. 13A. When the extendable pole 1310 and the information acquisition component 1210 are about to extend from the gantry 111, the lid 1320 may be lifted to allow the extension of the extendable pole 1310 as illustrated in FIG. 13C.

Figure 13D:
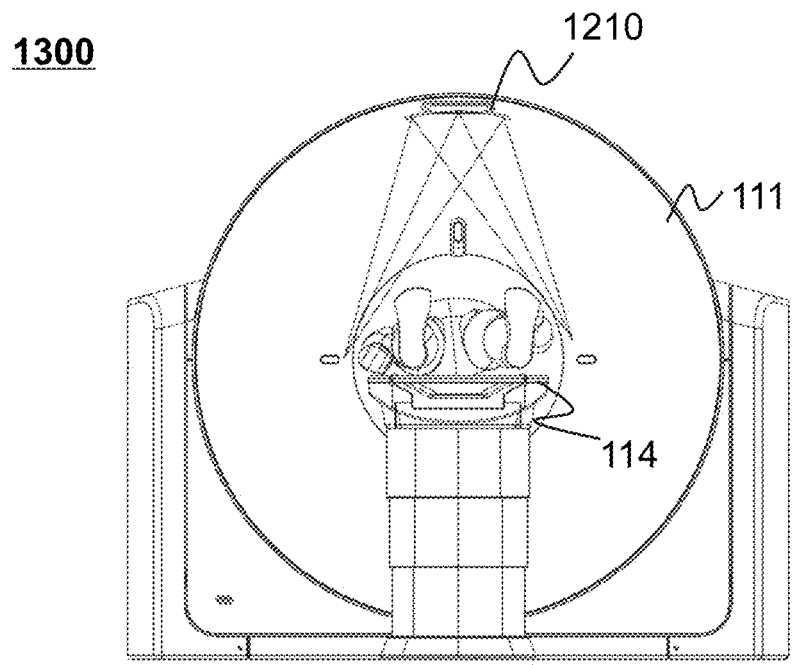
Figure 13E:
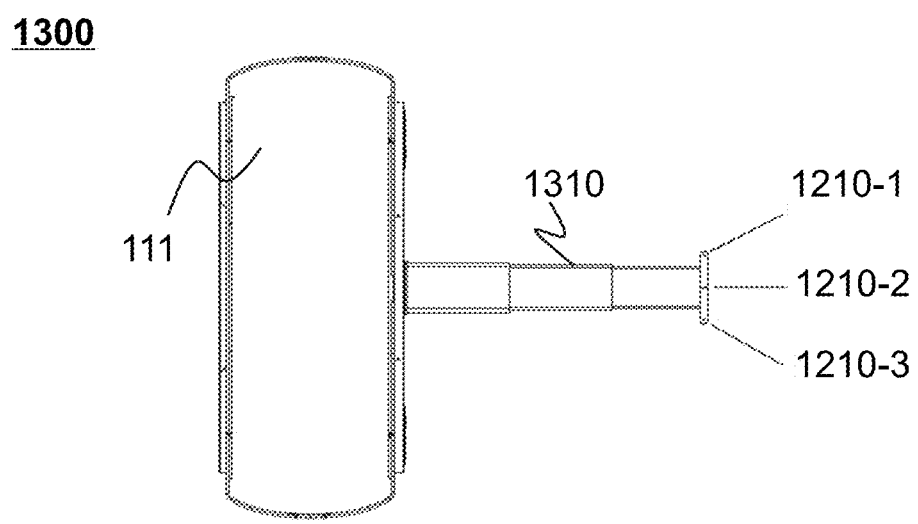

FIGS. 13D and 13E illustrate a front view and a top view of the imaging device 1300 when the information acquisition component 1210 is in use. As illustrated in FIG. 13E, the information acquisition component 1210 may include a plurality of sub-components, for example, 1210-1, 1210-2, and 1210-3. Each of the sub-components may be configured to acquire information associated with the subject from its perspective. Different sub-components may be of the same kind or different kinds of device. Different sub-components may collect the same kind or different kinds of information associated with the subject. In some embodiments, the sub-components may be arranged in an arc as illustrated in FIG. 13D so as to better collect information associated with the side body of the subject.

For example, the information acquisition component 1210 may include a plurality of cameras configured to capture the images of the structured light projected on the subject. The use of more than one camera may eliminate the image distortion, thus improving the quality of the captured images and increasing the speed of generating a 3D model of the subject. As another example, the information acquisition component 1210 may include a plurality of light pulse generators configured to emit the light pulses toward the subject. The sub-components 1210-1, 1210-2, and 1210-3 may be arranged in an arc from the view of FIG. 13D so that the light pulses may cover the side body of the subject.

It should be noted that the examples illustrated in FIGS. 13A to 13E and the descriptions thereof are merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the information acquisition component 1210 may be mounted at any position at the gantry 111, and/or be controlled by any suitable device other than the extendable pole 1310. As another example, the information acquisition component 1210 may include any number of sub-components. The sub-component(s) of the information acquisition component 1210 may be arranged in any suitable manner to provide different applications.

Figure 14A:
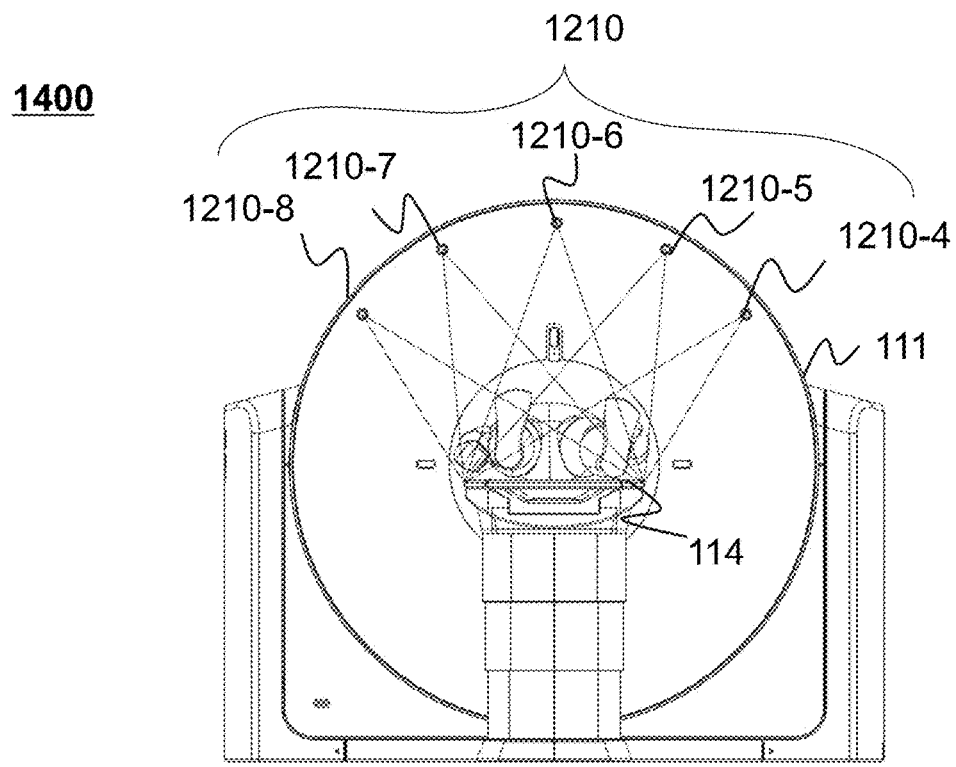
FIGS. 14A to 14B are schematic diagrams illustrating an exemplary imaging device according to some embodiments of the present disclosure.
Figure 14B:
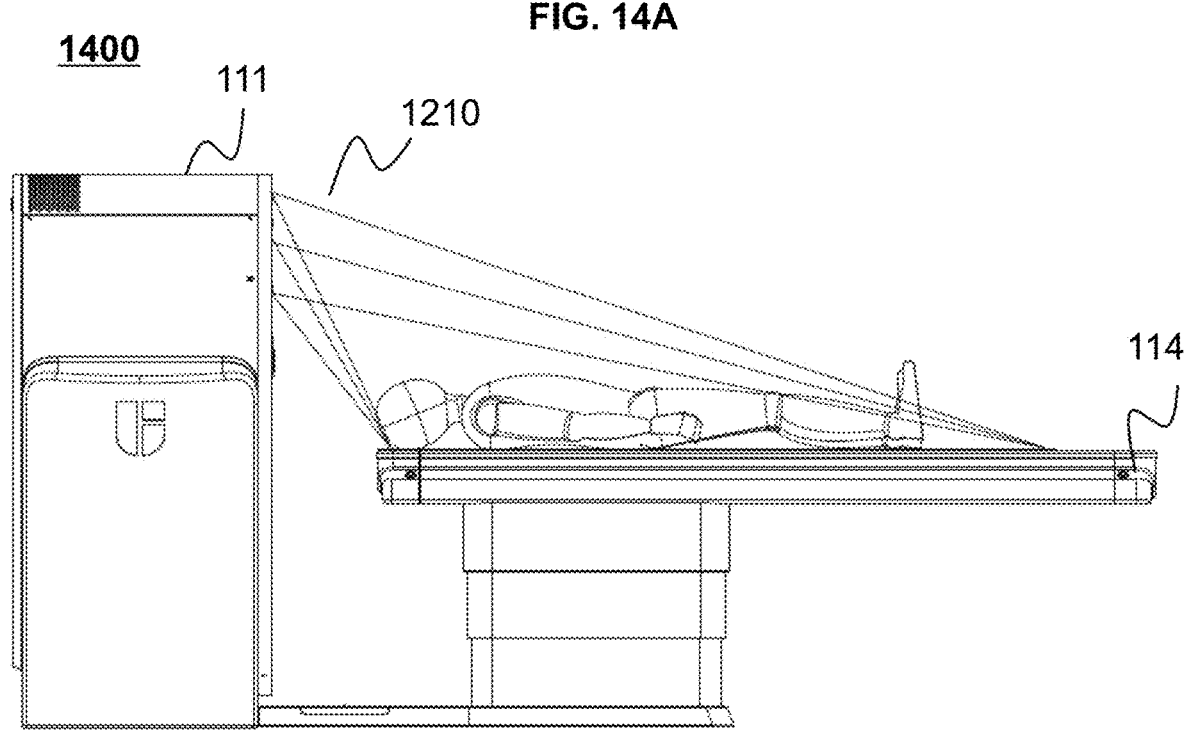
Figure 14C:
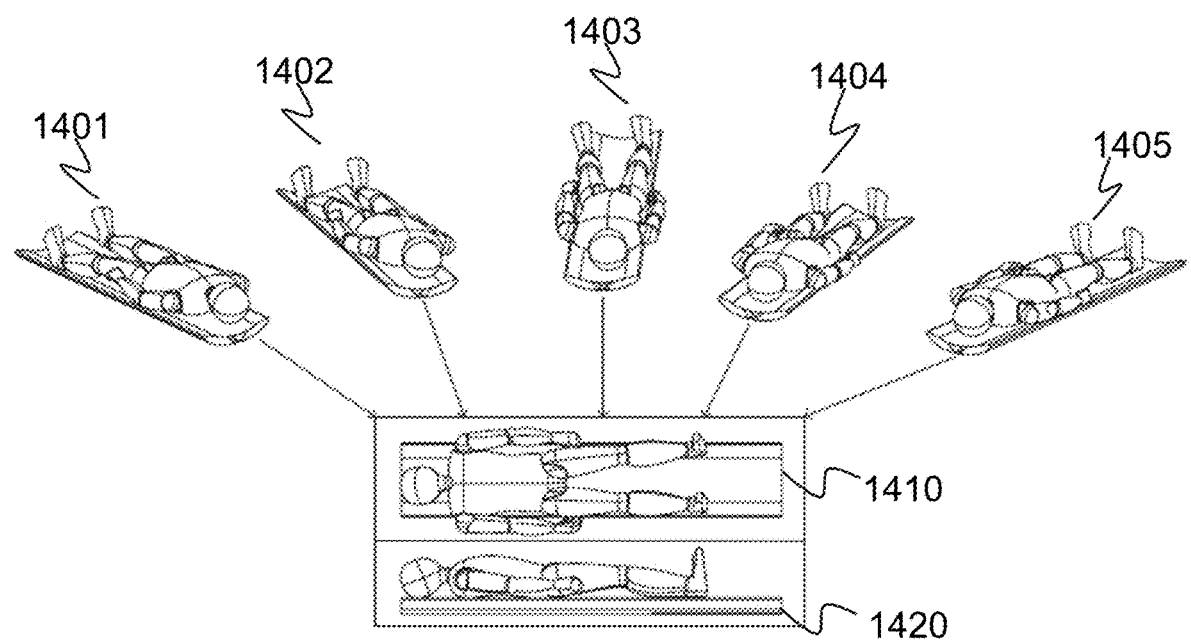
FIG. 14C illustrates exemplary images of a subject generated based on information acquisition components of an imaging device according to some embodiments of the present disclosure.

FIGS. 14A to 14B are schematic diagrams illustrating an exemplary imaging device 1400 according to some embodiments of the present disclosure. FIG. 14C illustrates exemplary images of a subject generated based on information acquisition components of the imaging device 1400 according to some embodiments of the present disclosure. The imaging device 1400 may be similar to the imaging device 1300 as described in FIGS. 13A to 13E, except for certain components or features.

As illustrated in FIGS. 14A and 14B, the imaging device 1400 may include a plurality of information acquisition components 1210, that is, 1210-4, 1210-5, 1210-6, 1210-7, and 1210-8. The plurality of information acquisition components 1210 may be configured at different positions at the gantry 111 to acquire information related to the subject from different perspectives. Merely by way of example, as illustrated in FIG. 14C, the information acquisition components 1210 may capture images (e.g., images 1401 to 1405) of the subject from different oblique angles. The model generation module 420 may generate a top view image 1410 of the subject based on the plurality of images 1401 to 1405 by, for example, using a matrix transformation technique. Additionally or alternatively, the model generation module 420 may further generate a side view image 1420 of the subject based on body thickness information of the subject.

In some embodiments, the information collected by the information acquisition components 1210 may further be used to generate a 3D model of the subject by implementing the process 1000 and/or the process 1100. In some embodiments, during an imaging process, the scanning table 114 may be moved along the X, Y and Z directions as illustrated in FIG. 1 to position the subject. The information acquisition components 1210 may acquire information related to the subject continuously or periodically during the movement of the scanning table 114. The 3D model of the subject may be generated and/or updated continuously or periodically, and the position of the ROI may be determined accordingly.

It should be noted that the example illustrated in FIGS. 14A to 14C and the above descriptions thereof are merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the imaging device 1400 may include any number of information acquisition components 1210. The information acquisition component(s) 1210 may be arranged in any suitable manner to provide different applications. In some embodiments, similar to the information acquisition component 1210 of the imaging device 1300, one or more information acquisition components 1210 of the imaging device 1400 may be retracted in and/or extended from the gantry 111 or a container mounted on the gantry 111.

It will be apparent to those skilled in the art that various changes and modifications can be made in the present disclosure without departing from the spirit and scope of the disclosure. In this manner, the present disclosure may be intended to include such modifications and variations if the modifications and variations of the present disclosure are within the scope of the appended claims and the equivalents thereof.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A system for generating a 3-dimensional (3D) model of a subject, comprising:
    a storage device storing a set of instructions; and
    at least one processor in communication with the storage device, wherein when executing the set of instructions, the at least one processor is configured to cause the system to:
        receive, from a flexible device configured with a plurality of position sensors, first position information related to a body contour of a subject with respect to a support, the flexible device being configured to conform to the body contour of the subject and independently movable with respect to the support, the support being configured to support the subject, the subject being placed between the support and the flexible device, wherein at least a portion of the plurality of position sensors are configured to transmit a signal passing through the subject toward the support or receive a signal passing through the subject from the support, and the first position information is determined based on the signals transmitted or received by the at least a portion of the plurality of position sensors; and
        generate, based on the first position information, the 3D model of the subject.

2. The system of claim 1, wherein:
    the flexible device includes a plurality of units arranged in an array, each of the plurality of units including one or more position sensors of the plurality of position sensors, and
    each pair of adjacent units of the plurality of units are connected to each other via a flexible connector.

3. The system of claim 2, wherein a unit of the plurality of units includes a first layer covering the one or more position sensors of the unit.

4. The system of claim 3, wherein:
    the unit of the plurality of units further includes a second layer, and
    the one or more position sensors of the unit are sandwiched between the first layer and the second layer.

5. The system of claim 1, wherein the support includes a pad provided on a scanning table of the imaging device.

6. The system of claim 1, wherein the at least one processor is further configured to cause the system to:
    determine, based on the 3D model of the subject, a position of a region of interest (ROI) inside the subject;
    obtain second position information of the subject with respect to the imaging device; and
    determine, based on the position of the ROI inside the subject and the second position information, the ROI of the subject.

7. The system of claim 6, wherein at least part of the second information is acquired from an image acquisition device or a plurality of pressure sensors configured in the support.

8. The system of claim 6, wherein to determine, based on the 3D model of the subject, the position of the ROI inside the subject, the at least one processor is configured to cause the system to:
    acquire information associated with thermal distribution of the subject; and
    determine, based on the 3D model of the subject and the information associated with thermal distribution of the subject, the position of the ROI inside the subject.

9. The system of claim 8, wherein at least one of the flexible device or the support includes one or more thermal sensors, and at least part of the information associated with thermal distribution of the subject is acquired from the one or more thermal sensors.

10. The system of claim 6, wherein to determine, based on the 3D model of the subject, the position of the ROI inside the subject, the at least one processor is configured to cause the system to:
   acquire physiological data related to the subject;
   acquire anatomical information associated with the subject; and
   determine, based on the 3D model of the subject, the physiological data, and anatomical information associated with the subject, the position of the ROI inside the subject.

11. The system of claim 10, wherein at least part of the physiological data is acquired from the support or be determined based on the 3D model of the subject.

12. The system of claim 1, wherein:
   the support includes a plurality of sensors to collect information related to the subject.

13. The system of claim 12, wherein:
   the plurality of sensors include at least one of a pressure sensor, a thermal sensor, or a position sensor.

14. The system of claim 1, wherein the first position information includes a plurality of distance measurements, each of the plurality of distance measurements representing a distance between one of the plurality of position sensors and the support.

15. A method implemented on at least one machine each of which has at least one processor and at least one storage device, the method comprising:
   receiving, from a flexible device configured with a plurality of position sensors, first position information related to a body contour of a subject with respect to a support, the flexible device being configured to conform to the body contour of the subject, the support being configured to support the subject and independently movable with respect to the support, the subject being placed between the support and the flexible device, wherein at least a portion of the plurality of position sensors are configured to transmit a signal passing through the subject toward the support or receive a signal passing through the subject from the support, and the first position information is determined based on the signals transmitted or received by the at least a portion of the plurality of position sensors; and
   generating, based on the first position information, the 3D model of the subject.

16. The method of claim 15, wherein:
   the support includes a plurality of sensors to collect information related to the subject.

17. The method of claim 16, wherein the generating, based on the first position information, the 3D model of the subject further includes:
   combining the first position information and the information related to the subject collected by the plurality of sensors; and
   generating, based on the combined information, the 3D model of the subject.

18. The method of claim 16, wherein:
   the plurality of sensors include at least one of a pressure sensor, a thermal sensor, or a position sensor.

19. The method of claim 15, wherein the support includes a pad provided on a scanning table of an imaging device.

20. A non-transitory computer readable medium comprising executable instructions that, when executed by at least one processor, cause the at least one processor to effectuate a method for image reconstruction, the method comprising:
   receiving, from a flexible device configured with a plurality of position sensors, first position information related to a body contour of a subject with respect to a support, the flexible device being configured to conform to the body contour of the subject, the support being configured to support the subject and independently movable with respect to the support, the subject being placed between the support and the flexible device, wherein at least a portion of the plurality of position sensors are configured to transmit a signal passing through the subject toward the support or receive a signal passing through the subject from the support, and the first position information is determined based on the signals transmitted or received by the at least a portion of the plurality of position sensors; and
   generating, based on the first position information, the 3D model of the subject.

* * * * *